(12) United States Patent
Vatannia et al.

(10) Patent No.: US 11,850,587 B2
(45) Date of Patent: Dec. 26, 2023

(54) HIGH DENSITY RESONANT TUNNELING

(71) Applicants: Vahid Vatannia, Stanford, CA (US); Saeid Vatannia, San Ramon, CA (US)

(72) Inventors: Vahid Vatannia, Stanford, CA (US); Saeid Vatannia, San Ramon, CA (US)

(73) Assignees: Vahid Vatannia, Stanford, CA (US); Saeid Vatannia, San Ramon, CA (US)

( * ) Notice: Subject to any disclaimer, the term of this patent is extended or adjusted under 35 U.S.C. 154(b) by 537 days.

(21) Appl. No.: 16/794,098

(22) Filed: Feb. 18, 2020

(65) Prior Publication Data
US 2020/0338553 A1 Oct. 29, 2020

Related U.S. Application Data

(63) Continuation of application No. PCT/US2018/046936, filed on Aug. 17, 2018.

(60) Provisional application No. 62/547,421, filed on Aug. 18, 2017.

(51) Int. Cl.
*B01L 3/00* (2006.01)
*C12Q 1/6869* (2018.01)

(52) U.S. Cl.
CPC ...... *B01L 3/502715* (2013.01); *C12Q 1/6869* (2013.01); *B01L 2300/06* (2013.01); *B01L 2300/0645* (2013.01); *B01L 2300/0681* (2013.01)

(58) Field of Classification Search
None
See application file for complete search history.

(56) References Cited

U.S. PATENT DOCUMENTS

| 5,640,010 | A | 6/1997 | Twerenbold | |
|---|---|---|---|---|
| 7,525,653 | B1 * | 4/2009 | Hug | G01N 21/65 356/417 |
| 2004/0144658 | A1 * | 7/2004 | Flory | G01N 33/48721 205/777.5 |
| 2004/0146430 | A1 * | 7/2004 | Dugas | G01N 33/48721 422/73 |

(Continued)

FOREIGN PATENT DOCUMENTS

| EP | 1574837 A1 | 9/2005 |
|---|---|---|
| WO | WO-2019036640 A1 | 2/2019 |

OTHER PUBLICATIONS

Albrecht. Electrochemical tunnelling sensors and their potential applications. Nature Communications 3:829 (May 8, 2012). 10 pages.

(Continued)

*Primary Examiner* — Matthew D Krcha
(74) *Attorney, Agent, or Firm* — Rahman LLC

(57) ABSTRACT

Methods and systems for macromolecular sequencing of one or a small number of a particular macromolecule are provided. The methods and systems generally operate by flowing a sample containing the macromolecule between a first electrode and a second electrode separated by a small gap. On one side of the gap, the first electrode is electrically coupled to an electron source that produces electrons with a narrow distribution of energies. On the other side of the gap, the second electrode is electrically coupled to an electric current sensor that detects electric current flowing across the gap from the first electrode to the second electrode.

17 Claims, 27 Drawing Sheets

(56) References Cited

U.S. PATENT DOCUMENTS

| | | | |
|---|---|---|---|
| 2005/0186629 A1* | 8/2005 | Barth | B81C 1/00087 |
| | | | 204/450 |
| 2005/0202444 A1* | 9/2005 | Zhu | C12Q 1/6825 |
| | | | 435/6.12 |
| 2008/0041733 A1* | 2/2008 | Hibbs | C12Q 1/6869 |
| | | | 204/403.01 |
| 2014/0131574 A1 | 5/2014 | Zewail et al. | |
| 2014/0154790 A1 | 6/2014 | Ono et al. | |

OTHER PUBLICATIONS

Bhadrachalam et al. Energy-filtered cold electron transport at room temperature. Nature Communications 5:4745 (Sep. 10, 2014). 8 pages.

EP18846772.4 Extended European Search Report dated Jun. 9, 2021.

PCT/US2018/046936 International Search Report and Written Opinion dated Dec. 21, 2018.

* cited by examiner

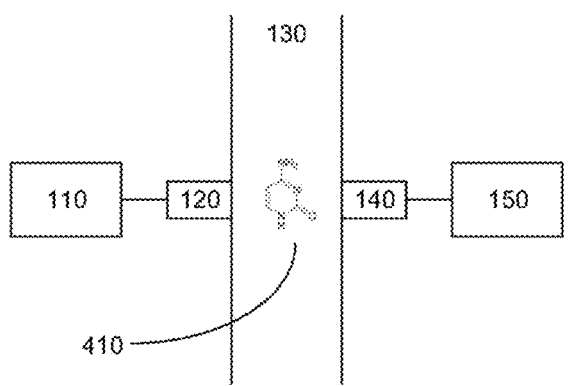 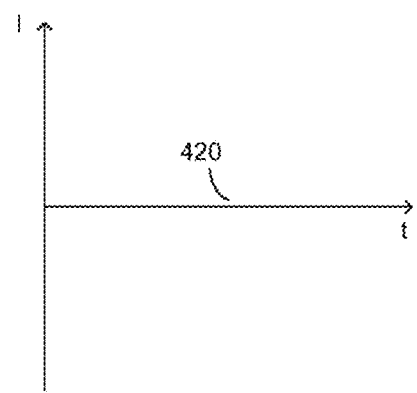
FIG. 4A                    FIG. 4B

1600

Non-optically directly detect individual subunits of a biopolymer to generate a sequence of the biopolymer. — 1610

HIGH DENSITY RESONANT TUNNELING

CROSS-REFERENCE

This application is a continuation application of International Application No. PCT/US18/046936, filed Aug. 17, 2018, which claims the benefit of U.S. Provisional Patent Application No. 62/547,421, filed Aug. 18, 2017, which applications are incorporated herein by reference in their entirety.

BACKGROUND

Macromolecular sequencing technologies have found broad application in the health sciences and others fields. Current sequencing technologies may operate by breaking a macromolecule, such as a nucleic acid or protein, into a large number of relatively short fragments. Each of these fragments is individually processed to determine the sequence of nucleotides or amino acid residues occurring on that fragment. Statistical models may be employed to determine where each sequenced fragment is located within the much larger whole macromolecule. These statistical methods may result in very large amounts of data and may only be capable of generating a list of most probable macromolecular sequences. These methods are often expensive, slow, and prone to error. They may result in a poor signal-to-noise (SNR) ratio, necessitating a relatively large number of macromolecules for accurate sequencing. Thus, there is a need for macromolecular sequencing techniques that allow inexpensive and rapid sequencing of a small number of macromolecules without resorting to statistical inference methods.

SUMMARY

Provided herein are methods and systems for macromolecular sequencing of one or a small number of a particular macromolecule. The methods and systems generally operate by flowing a sample containing the macromolecule between a first electrode and a second electrode separated by a small gap. On one side of the gap, the first electrode is electrically coupled to an electron source that produces electrons with a narrow distribution of energies. On the other side of the gap, the second electrode is electrically coupled to an electric current sensor that detects electric current flowing across the gap from the first electrode to the second electrode.

When a portion of a macromolecule (such as a particular nucleotide or a particular amino acid residue) with the specific electronic structure passes through the gap, electric current flows from the first electrode to the second electrode and is detected by the electric current sensor. At other times, no significant electric current flows through the gap. Thus, the flow of electric current across the gap as a function of time becomes a digital representation of the presence or non-presence of the portion of the macromolecule and an indication of its type. By changing the energy of the electrons emitted by the electron source, different portions of the macromolecule (such as a different nucleotide or a different amino acid residue) or different types of molecules may be detected. Thus, the sequence of the macromolecule may be determined by varying the energy of the electrons emitted by the electron source over time. Alternatively or in combination, the sequence of the macromolecule may be determined by employing multiple electron sources, multiple first and second electrode pairs, multiple current sensors, or any combination of these elements.

In an aspect, a system for molecular analysis may comprise a fluidic channel. The fluidic channel may be configured to receive a sample. The sample may comprise at least one molecule. The fluidic channel may include a first electrode and a second electrode. The first electrode may be separated from the second electrode by a gap. The gap may be dimensioned to permit the sample to pass through the gap.

The system may further comprise an electron source. The electron source may be configured to emit electrons with a central kinetic energy and a kinetic energy distribution. The kinetic energy distribution may have a full width at half maximum (FWHM) of no greater than 1 electron Volt (eV). The electron source may be electrically coupled to the first electrode.

The system may further comprise a current sensor. The current sensor may be electrically coupled to the second electrode. The current sensor may be configured to detect electric current passing from the first electrode to the second electrode.

The system may further comprise a controller. The controller may be coupled to the electron source and the current sensor. The controller may be configured to: (i) direct the electron source to emit the electrons to the first electrode and the gap upon flow of the sample through the gap, and (ii) use the current sensor to detect an electric current directed from the first electrode to the second electrode. When the at least one molecule passes through the gap, an electric current may flow from the first electrode to the second electrodes. The electric current may be detected by the current sensor. The detection of electric current by the current sensor may indicate a presence of the at least one molecule.

The electron source may comprise a thermal electron source and/or a quantum tunneling filter structure. The quantum tunneling filter structure may comprise a quantum well. The quantum tunneling filter structure may comprise a first metallic thin film, a dielectric thin film, and a second metallic thin film. The first and second metallic thin films may comprise a material selected from the group consisting of platinum, gold, silver, copper, titanium nitride, and cobalt silicide. The dielectric thin film may comprise a material selected from the group consisting of silicon oxide ($SiO_x$), aluminum oxide ($Al_xO_y$), silicon nitride ($Si_3N_4$), and calcium fluoride (CaF). The quantum tunneling filter structure may comprise a double quantum well. The quantum tunneling filter structure may comprise a first metallic thin film, a first dielectric thin film, a second metallic thin film, a second dielectric thin film, and a third metallic thin film. The first, second, and third metallic thin films may comprise a material selected from the group consisting of platinum, gold, silver, copper, titanium nitride, and cobalt silicide. The first and second dielectric thin film may comprise a material selected from the group consisting of silicon oxide ($SiO_x$), aluminum oxide ($Al_xO_y$), silicon nitride ($Si_3N_4$), and calcium fluoride (CaF). The quantum tunneling filter structure may comprise a triple quantum well. The quantum tunneling filter structure may comprise a first metallic, thin film, a first dielectric thin film, a second metallic thin film, a second dielectric thin film, a third metallic thin film, a third dielectric thin film, and a fourth metallic thin film. The first, second, third and fourth metallic thin films may comprise a material selected from the group consisting of platinum, gold, silver, copper, titanium nitride, and cobalt silicide. The first, second, and third dielectric thin films may comprise a material selected from the group consisting of silicon oxide ($SiO_x$), aluminum oxide ($Al_xO_y$), silicon nitride ($Si_3N_4$), and calcium fluoride (CaF). The quantum tunneling filter structure may comprise a multi-quantum well.

The controller may be configured to bias the first electrode by a first electric potential and to bias the second electrode by a second electric potential. The first and second electric potentials may determine the central kinetic energy of the emitted electrons.

The electrons may be emitted with a kinetic energy distribution having a full width at half maximum (FWHM) of no greater than 0.1 eV. The electrons may be emitted with a kinetic energy distribution having a full width at half maximum (FWHM) of no greater than 0.05 eV. The electrons may be emitted with a kinetic energy distribution having a full width at half maximum (FWHM) of no greater than 0.01 eV. The electrons may be emitted with a kinetic energy distribution having a full width at half maximum (FWHM) of no greater than 0.005 eV. The electrons may be emitted with a kinetic energy distribution having a full width at half maximum (FWHM) of no greater than 1 meV. The electrons may be emitted with a kinetic energy distribution having a full width at half maximum (FWHM) of no greater than 0.5 meV. The electrons may be emitted with a kinetic energy distribution having a full width at half maximum (FWHM) of no greater than 0.1 meV. The electrons may be emitted with a kinetic energy distribution having a full width at half maximum (FWHM) of no greater than 0.05 meV. The electrons may be emitted with a kinetic energy distribution having a full width at half maximum (FWHM) of no greater than 0.01 eV.

The electrons may be emitted with a kinetic energy distribution having a central energy that corresponds to a highest occupied molecular orbital (HOMO) to lowest unoccupied molecular orbital (LUMO) transition energy of the at least one molecule or a portion of the at least one molecule. The electrons may be emitted with a kinetic energy distribution having a central energy that corresponds to a HOMO to LUMO transition energy of a nucleoside, nucleotide, nucleoside pair, or nucleotide pair of the sample. The electrons may be emitted with a kinetic energy distribution having a central energy that corresponds to a HOMO to LUMO transition energy of adenine. The electrons may be emitted with a kinetic energy distribution having a central energy that corresponds to a HOMO to LUMO transition energy of cytosine. The electrons may be emitted with a kinetic energy distribution having a central energy that corresponds to a HOMO to LUMO transition energy of guanine. The electrons may be emitted with a kinetic energy distribution having a central energy that corresponds to a HOMO to LUMO transition energy of thymine. The electrons may be emitted with a kinetic energy distribution having a central energy that corresponds to a HOMO to LUMO transition energy of uracil. The electrons may be emitted with a kinetic energy distribution having a central energy that corresponds to a HOMO to LUMO transition energy of adenine:thymine. The electrons may be emitted with a kinetic energy distribution having a central energy that corresponds to a HOMO to LUMO transition energy of cytosine:guanine.

The electrons may be emitted with a kinetic energy distribution having a central energy that corresponds to a HOMO to LUMO transition energy of a methylated nucleoside, methylated nucleotide, methylated nucleoside pair, or methylated nucleotide pair.

The electrons may be emitted with a kinetic energy distribution having a central energy that corresponds to a HUMO to LUMO transition energy of an amino acid. The electrons may be emitted with a kinetic energy distribution having a central energy that corresponds to a HOMO to LUMO transition energy of alanine. The electrons may be emitted with a kinetic energy distribution having a central energy that corresponds to a HOMO to LUMO transition energy of arginine. The electrons may be emitted with a kinetic energy distribution having a central energy that corresponds to a HOMO to LUMO transition energy of asparagine. The electrons may be emitted with a kinetic energy distribution having a central energy that corresponds to a HOMO to LUMO transition energy of aspartic acid. The electrons may be emitted with a kinetic energy distribution having a central energy that corresponds to a HOMO to LUMO transition energy of cysteine. The electrons may be emitted with a kinetic energy distribution having a central energy that corresponds to a HOMO to LUMO transition energy of glutamine. The electrons may be emitted with a kinetic energy distribution having a central energy that corresponds to a HOMO to LUMO transition energy of glutamic acid. The electrons may be emitted with a kinetic energy distribution having a central energy that corresponds to a HOMO to LUMO transition energy of glycine. The electrons may be emitted with a kinetic energy distribution having a central energy that corresponds to a HOMO to LUMO transition energy of histidine. The electrons may be emitted with a kinetic energy distribution having a central energy that corresponds to a HOMO to LUMO transition energy of isoleucine. The electrons may be emitted with a kinetic energy distribution having a central energy that corresponds to a HOMO to LUMO transition energy of leucine. The electrons may be emitted with a kinetic energy distribution having a central energy that corresponds to a HOMO to LUMO transition energy of lysine. The electrons may be emitted with a kinetic energy distribution having a central energy that corresponds to a HOMO to LUMO transition energy of methionine. The electrons may be emitted with a kinetic energy distribution having a central energy that corresponds to a HOMO to LUMO transition energy of phenylalanine. The electrons may be emitted with a kinetic energy distribution having a central energy that corresponds to a HOMO to LUMO transition energy of proline. The electrons may be emitted with a kinetic energy distribution having a central energy that corresponds to a HOMO to LUMO transition energy of serine. The electrons may be emitted with a kinetic energy distribution having a central energy that corresponds to a HOMO to LUMO transition energy of threonine. The electrons may be emitted with a kinetic energy distribution having a central energy that corresponds to a HOMO to LUMO transition energy of tryptophan. The electrons may be emitted with a kinetic energy distribution having a central energy that corresponds to a HOMO to LUMO transition energy of tyrosine. The electrons may be emitted with a kinetic energy distribution having a central energy that corresponds to a HOMO to LUMO transition energy of valine.

The electrons may be emitted with a kinetic energy distribution having a central energy that corresponds to a HUMO to LUMO transition energy of a sugar.

The width of the fluidic channel may be at least 1 nanometers (nm). The width of the fluidic channel may be at least 2 nm. The width of the fluidic channel may be at least 3 nm. The width of the fluidic channel may be at least 4 nm. The width of the fluidic channel may be at least 5 nm. The width of the fluidic channel may be at least 6 nm. The width of the fluidic channel may be at least 7 nm. The width of the fluidic channel may be at least 8 nm. The width of the fluidic channel may be at least 9 nm. The width of the fluidic channel may be at least 10 nm.

The current sensor may comprise: (i) a current to voltage conversion circuit, (ii) a buffer, (iii) a sample and hold circuit, and (iv) an analog-to-digital (ADC) converter. The current sensor may be configured to detect a nucleoside, nucleotide, nucleoside pair, or nucleotide pair of only a single type. The current sensor may be configured to detect adenine. The current sensor may be configured to detect cytosine. The current sensor may be configured to detect guanine. The current sensor may be configured to detect thymine. The current sensor may be configured to detect adenine:thymine. The current sensor may be configured to detect cytosine:guanine. The current sensor may be configured to detect a methylated nucleoside, methylated nucleotide, methylated nucleoside pair, or methylated nucleotide pair of a single type. The current sensor may be configured to detect an amino acid of a single type. The current sensor may be configured to detect a sugar of a single type. The current sensor may comprise a plurality of current sub-sensors. Each sub-sensor of the plurality may be configured to detect a nucleoside, nucleotide, nucleoside pair, or nucleotide pair of a single type. Each sub-sensor of the plurality may be configured to detect a methylated nucleoside, methylated nucleotide, methylated nucleoside pair, or methylated nucleotide pair of a single type. Each sub-sensor of the plurality may be configured to detect an amino acid of a single type. Each sub-sensor of the plurality may be configured to detect a sugar of a single type.

The current sensor may be configured to detect nucleosides, nucleotides, nucleoside pairs, or nucleotide pairs of a plurality of types, which plurality is less than all types of nucleosides, nucleotides, nucleoside pairs, or nucleotide pairs. The current sensor may be configured to detect methylated nucleosides, methylated nucleotides, methylated nucleoside pairs, or methylated nucleotide pairs of a plurality of types, which plurality is less than all types of methylated nucleotides, methylated nucleoside pairs, or methylated nucleotide pairs. The current sensor may be configured to detect amino acids of a plurality of types, which plurality is less than all types of amino acids. The current sensor may be configured to detect sugars of a plurality of types, which plurality is less than all types of sugars.

The system may further comprise a positive electrophoresis electrode located at a first position along a length of the channel and a negative electrophoresis electrode located at a second position along the length of the channel, the positive and negative electrophoresis electrodes configured to advance the sample along all or a part of the length of the channel by electrophoresis.

The sample may be a polymer and the at least one molecule may be a monomer.

In another aspect, a method for molecular analysis may comprise the operations of: (a) activating a system comprising (i) a fluidic channel, wherein the fluidic channel includes a first electrode and a second electrode separated from the second electrode by a gap dimensioned to permit the sample to pass through the gap; (ii) an electron source electrically coupled to the first electrode; and (iii) a current sensor electrically coupled to the second electrode and configured to detect electric current passing from the first electrode to the second electrode; (b) directing the electron source to emit the electrons to the first electrode and the gap upon flow of the sample through the gap; and (c) using the current sensor to detect an electric current directed from the first electrode to the second electrode.

When the at least one molecule passes through the gap, an electric current may flow from the first electrode to the second electrode. The electric current may be detected by the current sensor. The detected electric current may indicate a presence of the at least one molecule.

The channel may be configured to receive a sample. The sample may comprise at least one molecule.

The electron source may be configured to emit electrons with a central kinetic energy and a kinetic energy distribution. The kinetic energy distribution may have a full width at half maximum (FWHM) of no greater than 1 electron Volt (eV).

The electron source may comprise a thermal electron source and a quantum tunneling filter structure. The quantum tunneling filter structure may comprise a quantum well. The quantum tunneling filter structure may comprise a first metallic thin film, a dielectric thin film, and a second metallic thin film. The first and second metallic thin films may comprise a material selected from the group consisting of platinum, gold, silver, copper, titanium nitride, and cobalt silicide. The dielectric thin film may comprise a material selected from the group consisting of silicon oxide ($SiO_x$), aluminum oxide ($Al_xO_y$), silicon nitride ($Si_3N_4$), and calcium fluoride (CaF). The quantum tunneling filter structure may comprise a double quantum well. The quantum tunneling filter structure may comprise a first metallic thin film, a first dielectric thin film, a second metallic thin film, a second dielectric thin film, and a third metallic thin film. The first, second, and third metallic thin films may comprise a material selected from the group consisting of platinum, gold, silver, copper, titanium nitride, and cobalt silicide. The first and second dielectric thin film may comprise a material selected from the group consisting of silicon oxide ($SiO_x$), aluminum oxide ($Al_xO_y$), silicon nitride ($Si_3N_4$), and calcium fluoride (CaF). The quantum tunneling filter structure may comprise a triple quantum well. The quantum tunneling filter structure may comprise a first metallic, thin film, a first dielectric thin film, a second metallic thin film, a second dielectric thin film, a third metallic thin film, a third dielectric thin film, and a fourth metallic thin film. The first, second, third and fourth metallic thin films may comprise a material selected from the group consisting of platinum, gold, silver, copper, titanium nitride, and cobalt silicide. The first, second, and third dielectric thin films may comprise a material selected from the group consisting of silicon oxide ($SiO_x$), aluminum oxide ($Al_xO_y$), silicon nitride ($Si_3N_4$), and calcium fluoride (CaF). The quantum tunneling filter structure may comprise a multi-quantum well.

The controller may be configured to bias the first electrode by a first electric potential and to bias the second electrode by a second electric potential. The first and second electric potentials may determine the central kinetic energy of the emitted electrons.

The electrons may be emitted with a kinetic energy distribution having a full width at half maximum (FWHM) of no greater than 0.1 eV. The electrons may be emitted with a kinetic energy distribution having a full width at half maximum (FWHM) of no greater than 0.05 eV. The electrons may be emitted with a kinetic energy distribution having a full width at half maximum (FWHM) of no greater than 0.01 eV. The electrons may be emitted with a kinetic energy distribution having a full width at half maximum (FWHM) of no greater than 0.005 eV. The electrons may be emitted with a kinetic energy distribution having a full width at half maximum (FWHM) of no greater than 1 meV. The electrons may be emitted with a kinetic energy distribution having a full width at half maximum (FWHM) of no greater than 0.5 meV. The electrons may be emitted with a kinetic energy distribution having a full width at half maximum (FWHM) of no greater than 0.1 meV. The electrons may be emitted with a kinetic energy distribution having a full width at half maximum (FWHM) of no greater than 0.05 meV. The electrons may be emitted with a kinetic energy distribution having a full width at half maximum (FWHM) of no greater than 0.01 eV.

The electrons may be emitted with a kinetic energy distribution having a central energy that corresponds to a highest occupied molecular orbital (HOMO) to lowest unoccupied molecular orbital (LUMO) transition energy of the at least one molecule or a portion of the at least one molecule. The electrons may be emitted with a kinetic energy distribution having a central energy that corresponds to a HOMO to LUMO transition energy of a nucleoside, nucleotide, nucleoside pair, or nucleotide pair of the sample. The electrons may be emitted with a kinetic energy distribution having a central energy that corresponds to a HOMO to LUMO transition energy of adenine. The electrons may be emitted with a kinetic energy distribution having a central energy that corresponds to a HOMO to LUMO transition energy of cytosine. The electrons may be emitted with a kinetic energy distribution having a central energy that corresponds to a HOMO to LUMO transition energy of guanine. The electrons may be emitted with a kinetic energy distribution having a central energy that corresponds to a HOMO to LUMO transition energy of thymine. The electrons may be emitted with a kinetic energy distribution having a central energy that corresponds to a HOMO to LUMO transition energy of uracil. The electrons may be emitted with a kinetic energy distribution having a central energy that corresponds to a HOMO to LUMO transition energy of adenine:thymine. The electrons may be emitted with a kinetic energy distribution having a central energy that corresponds to a HOMO to LUMO transition energy of cytosine:guanine.

The electrons may be emitted with a kinetic energy distribution having a central energy that corresponds to a HOMO to LUMO transition energy of a methylated nucleoside, methylated nucleotide, methylated nucleoside pair, or methylated nucleotide pair.

The electrons may be emitted with a kinetic energy distribution having a central energy that corresponds to a HUMO to LUMO transition energy of an amino acid. The electrons may be emitted with a kinetic energy distribution having a central energy that corresponds to a HOMO to LUMO transition energy of alanine. The electrons may be emitted with a kinetic energy distribution having a central energy that corresponds to a HOMO to LUMO transition energy of arginine. The electrons may be emitted with a kinetic energy distribution having a central energy that corresponds to a HOMO to LUMO transition energy of asparagine. The electrons may be emitted with a kinetic energy distribution having a central energy that corresponds to a HOMO to LUMO transition energy of aspartic acid. The electrons may be emitted with a kinetic energy distribution having a central energy that corresponds to a HOMO to LUMO transition energy of cysteine. The electrons may be emitted with a kinetic energy distribution having a central energy that corresponds to a HOMO to LUMO transition energy of glutamine. The electrons may be emitted with a kinetic energy distribution having a central energy that corresponds to a HOMO to LUMO transition energy of glutamic acid. The electrons may be emitted with a kinetic energy distribution having a central energy that corresponds to a HOMO to LUMO transition energy of glycine. The electrons may be emitted with a kinetic energy distribution having a central energy that corresponds to a HOMO to LUMO transition energy of histidine. The electrons may be emitted with a kinetic energy distribution having a central energy that corresponds to a HOMO to LUMO transition energy of isoleucine. The electrons may be emitted with a kinetic energy distribution having a central energy that corresponds to a HOMO to LUMO transition energy of leucine. The electrons may be emitted with a kinetic energy distribution having a central energy that corresponds to a HOMO to LUMO transition energy of lysine. The electrons may be emitted with a kinetic energy distribution having a central energy that corresponds to a HOMO to LUMO transition energy of methionine. The electrons may be emitted with a kinetic energy distribution having a central energy that corresponds to a HOMO to LUMO transition energy of phenylalanine. The electrons may be emitted with a kinetic energy distribution having a central energy that corresponds to a HOMO to LUMO transition energy of proline. The electrons may be emitted with a kinetic energy distribution having a central energy that corresponds to a HOMO to LUMO transition energy of serine. The electrons may be emitted with a kinetic energy distribution having a central energy that corresponds to a HOMO to LUMO transition energy of threonine. The electrons may be emitted with a kinetic energy distribution having a central energy that corresponds to a HOMO to LUMO transition energy of tryptophan. The electrons may be emitted with a kinetic energy distribution having a central energy that corresponds to a HOMO to LUMO transition energy of tyrosine. The electrons may be emitted with a kinetic energy distribution having a central energy that corresponds to a HOMO to LUMO transition energy of valine.

The electrons may be emitted with a kinetic energy distribution having a central energy that corresponds to a HUMO to LUMO transition energy of a sugar.

The width of the fluidic channel may be at least 1 nanometers (nm). The width of the fluidic channel may be at least 2 nm. The width of the fluidic channel may be at least 3 nm. The width of the fluidic channel may be at least 4 nm. The width of the fluidic channel may be at least 5 nm. The width of the fluidic channel may be at least 6 nm. The width of the fluidic channel may be at least 7 nm. The width of the fluidic channel may be at least 8 nm. The width of the fluidic channel may be at least 9 nm. The width of the fluidic channel may be at least 10 nm.

The current sensor may comprise: (i) a current to voltage conversion circuit, (ii) a buffer, (iii) a sample and hold circuit, and (iv) an analog-to-digital (ADC) converter. The current sensor may be configured to detect a nucleoside, nucleotide, nucleoside pair, or nucleotide pair of only a single type. The current sensor may be configured to detect adenine. The current sensor may be configured to detect cytosine. The current sensor may be configured to detect guanine. The current sensor may be configured to detect thymine. The current sensor may be configured to detect adenine:thymine. The current sensor may be configured to detect cytosine:guanine. The current sensor may be configured to detect a methylated nucleoside, methylated nucleotide, methylated nucleoside pair, or methylated nucleotide pair of a single type. The current sensor may be configured to detect an amino acid of a single type. The current sensor may be configured to detect a sugar of a single type. The current sensor may comprise a plurality of current sub-sensors. Each sub-sensor of the plurality may be configured to detect a nucleoside, nucleotide, nucleoside pair, or nucleotide pair of a single type. Each sub-sensor of the plurality may be configured to detect a methylated nucleoside, methylated nucleotide, methylated nucleoside pair, or methylated nucleotide pair of a single type. Each sub-sensor of the plurality may be configured to detect an amino acid of a single type. Each sub-sensor of the plurality may be configured to detect a sugar of a single type.

The current sensor may be configured to detect nucleosides, nucleotides, nucleoside pairs, or nucleotide pairs of a plurality of types, which plurality is less than all types of nucleosides, nucleotides, nucleoside pairs, or nucleotide pairs. The current sensor may be configured to detect methylated nucleosides, methylated nucleotides, methylated nucleoside pairs, or methylated nucleotide pairs of a plurality of types, which plurality is less than all types of methylated nucleotides, methylated nucleoside pairs, or methylated nucleotide pairs. The current sensor may be configured to detect amino acids of a plurality of types, which plurality is less than all types of amino acids. The current sensor may be configured to detect sugars of a plurality of types, which plurality is less than all types of sugars.

The system may further comprise a positive electrophoresis electrode located at a first position along a length of the channel and a negative electrophoresis electrode located at a second position along the length of the channel, the positive and negative electrophoresis electrodes configured to advance the sample along all or a part of the length of the channel by electrophoresis. The method may further comprise advancing the sample along all or a part of the length of the channel by electrophoresis.

The method may further comprise detecting a time-ordered plurality of electric currents over a plurality of points in time, each electric current of the plurality associated with a different point in time, wherein the time-ordered plurality of electric currents is indicative of a presence or absence of the at least one molecule or the portion of the at least one molecule at different points in time as the at least one molecule or the portion of the at least one molecule passes through the current sensor. The method may further comprise subjecting the time-ordered plurality of electric currents to a window search procedure to determine points in time at which the at least one molecule or the portion of the at least one molecule passed through the current sensor. The window search procedure may comprise detecting and comparing a first window of time-ordered electric currents to a second window of time-ordered electric currents, wherein a change in electric current between the first window and the second window is indicative of a movement of the at least one molecule or the portion of the at least one molecule into or out of the current sensor. The first and second windows may differ by a single point in time. The size of the first and second windows may correspond to a number of portions of the at least one molecule passing through the current sensor at any point in time. The method may further comprise comparing all possible windows differing by a single point in time.

The sample may be a polymer and the at least one molecule may be a monomer.

In another aspect, a non-transitory computer-readable medium may comprise machine-executable code that, upon execution by one or more computer processors, implements a method for molecular analysis. The method may comprise the operations of: (a) activating a system comprising (i) a fluidic channel, wherein the fluidic channel includes a first electrode and a second electrode separated from the second electrode by a gap dimensioned to permit the sample to pass through the gap; (ii) an electron source electrically coupled to the first electrode; and (iii) a current sensor electrically coupled to the second electrode and configured to detect electric current passing from the first electrode to the second electrode; (b) directing the electron source to emit the electrons to the first electrode and the gap upon flow of the sample through the gap; and (c) using the current sensor to detect an electric current directed from the first electrode to the second electrode.

When the at least one molecule passes through the gap, an electric current may flow from the first electrode to the second electrode. The electric current may be detected by the current sensor. The detected electric current may indicate a presence of the at least one molecule.

The channel may be configured to receive a sample. The sample may comprise at least one molecule.

The electron source may be configured to emit electrons with a central kinetic energy and a kinetic energy distribution. The kinetic energy distribution may have a full width at half maximum (FWHM) of no greater than 1 electron Volt (eV).

The electron source may comprise a thermal electron source and a quantum tunneling filter structure. The quantum tunneling filter structure may comprise a quantum well. The quantum tunneling filter structure may comprise a first metallic thin film, a dielectric thin film, and a second metallic thin film. The first and second metallic thin films may comprise a material selected from the group consisting of platinum, gold, silver, copper, titanium nitride, and cobalt silicide. The dielectric thin film may comprise a material selected from the group consisting of silicon oxide ($SiO_x$), aluminum oxide ($Al_xO_y$), and calcium fluoride (CaF). The quantum tunneling filter structure may comprise a double quantum well. The quantum tunneling filter structure may comprise a first metallic thin film, a first dielectric thin film, a second metallic thin film, a second dielectric thin film, and a third metallic thin film. The first, second, and third metallic thin films may comprise a material selected from the group consisting of platinum, gold, silver, copper, titanium nitride, and cobalt silicide. The first and second dielectric thin film may comprise a material selected from the group consisting of silicon oxide ($SiO_x$), aluminum oxide ($Al_xO_y$), silicon nitride ($Si_3N_4$), and calcium fluoride (CaF). The quantum tunneling filter structure may comprise a triple quantum well. The quantum tunneling filter structure may comprise a first metallic, thin film, a first dielectric thin film, a second metallic thin film, a second dielectric thin film, a third metallic thin film, a third dielectric thin film, and a fourth metallic thin film. The first, second, third and fourth metallic thin films may comprise a material selected from the group consisting of platinum, gold, silver, copper, titanium nitride, and cobalt silicide. The first, second, and third dielectric thin films may comprise a material selected from the group consisting of silicon oxide ($SiO_x$), aluminum oxide ($Al_xO_y$), silicon nitride ($Si_3N_4$), and calcium fluoride (CaF). The quantum tunneling filter structure may comprise a multi-quantum well.

The controller may be configured to bias the first electrode by a first electric potential and to bias the second electrode by a second electric potential. The first and second electric potentials may determine the central kinetic energy of the emitted electrons.

The electrons may be emitted with a kinetic energy distribution having a full width at half maximum (FWHM) of no greater than 0.1 eV. The electrons may be emitted with a kinetic energy distribution having a full width at half maximum (FWHM) of no greater than 0.05 eV. The electrons may be emitted with a kinetic energy distribution having a full width at half maximum (FWHM) of no greater than 0.01 eV. The electrons may be emitted with a kinetic energy distribution having a full width at half maximum (FWHM) of no greater than 0.005 eV. The electrons may be emitted with a kinetic energy distribution having a full width at half maximum (FWHM) of no greater than 1 meV. The electrons may be emitted with a kinetic energy distribution having a full width at half maximum (FWHM) of no greater than 0.5 meV. The electrons may be emitted with a kinetic energy distribution having a full width at half maximum (FWHM) of no greater than 0.1 meV. The electrons may be emitted with a kinetic energy distribution having a full width at half maximum (FWHM) of no greater than 0.05 meV. The electrons may be emitted with a kinetic energy distribution having a full width at half maximum (FWHM) of no greater than 0.01 eV.

The electrons may be emitted with a kinetic energy distribution having a central energy that corresponds to a highest occupied molecular orbital (HOMO) to lowest unoccupied molecular orbital (LUMO) transition energy of the at least one molecule or a portion of the at least one molecule. The electrons may be emitted with a kinetic energy distribution having a central energy that corresponds to a HOMO to LUMO transition energy of a nucleoside, nucleotide, nucleoside pair, or nucleotide pair of the sample. The electrons may be emitted with a kinetic energy distribution having a central energy that corresponds to a HOMO to LUMO transition energy of adenine. The electrons may be emitted with a kinetic energy distribution having a central energy that corresponds to a HOMO to LUMO transition energy of cytosine. The electrons may be emitted with a kinetic energy distribution having a central energy that corresponds to a HOMO to LUMO transition energy of guanine. The electrons may be emitted with a kinetic energy distribution having a central energy that corresponds to a HOMO to LUMO transition energy of thymine. The electrons may be emitted with a kinetic energy distribution having a central energy that corresponds to a HOMO to LUMO transition energy of uracil. The electrons may be emitted with a kinetic energy distribution having a central energy that corresponds to a HOMO to LUMO transition energy of adenine:thymine. The electrons may be emitted with a kinetic energy distribution having a central energy that corresponds to a HOMO to LUMO transition energy of cytosine:guanine.

The electrons may be emitted with a kinetic energy distribution having a central energy that corresponds to a HOMO to LUMO transition energy of a methylated nucleoside, methylated nucleotide, methylated nucleoside pair, or methylated nucleotide pair.

The electrons may be emitted with a kinetic energy distribution having a central energy that corresponds to a HUMO to LUMO transition energy of an amino acid. The electrons may be emitted with a kinetic energy distribution having a central energy that corresponds to a HOMO to LUMO transition energy of alanine. The electrons may be emitted with a kinetic energy distribution having a central energy that corresponds to a HOMO to LUMO transition energy of arginine. The electrons may be emitted with a kinetic energy distribution having a central energy that corresponds to a HOMO to LUMO transition energy of asparagine. The electrons may be emitted with a kinetic energy distribution having a central energy that corresponds to a HOMO to LUMO transition energy of aspartic acid. The electrons may be emitted with a kinetic energy distribution having a central energy that corresponds to a HOMO to LUMO transition energy of cysteine. The electrons may be emitted with a kinetic energy distribution having a central energy that corresponds to a HOMO to LUMO transition energy of glutamine. The electrons may be emitted with a kinetic energy distribution having a central energy that corresponds to a HOMO to LUMO transition energy of glutamic acid. The electrons may be emitted with a kinetic energy distribution having a central energy that corresponds to a HOMO to LUMO transition energy of glycine. The electrons may be emitted with a kinetic energy distribution having a central energy that corresponds to a HOMO to LUMO transition energy of histidine. The electrons may be emitted with a kinetic energy distribution having a central energy that corresponds to a HOMO to LUMO transition energy of isoleucine. The electrons may be emitted with a kinetic energy distribution having a central energy that corresponds to a HOMO to LUMO transition energy of leucine. The electrons may be emitted with a kinetic energy distribution having a central energy that corresponds to a HOMO to LUMO transition energy of lysine. The electrons may be emitted with a kinetic energy distribution having a central energy that corresponds to a HOMO to LUMO transition energy of methionine. The electrons may be emitted with a kinetic energy distribution having a central energy that corresponds to a HOMO to LUMO transition energy of phenylalanine. The electrons may be emitted with a kinetic energy distribution having a central energy that corresponds to a HOMO to LUMO transition energy of proline. The electrons may be emitted with a kinetic energy distribution having a central energy that corresponds to a HOMO to LUMO transition energy of serine. The electrons may be emitted with a kinetic energy distribution having a central energy that corresponds to a HOMO to LUMO transition energy of threonine. The electrons may be emitted with a kinetic energy distribution having a central energy that corresponds to a HOMO to LUMO transition energy of tryptophan. The electrons may be emitted with a kinetic energy distribution having a central energy that corresponds to a HOMO to LUMO transition energy of tyrosine. The electrons may be emitted with a kinetic energy distribution having a central energy that corresponds to a HOMO to LUMO transition energy of valine.

The electrons may be emitted with a kinetic energy distribution having a central energy that corresponds to a HUMO to LUMO transition energy of a sugar.

The width of the fluidic channel may be at least 1 nanometers (nm). The width of the fluidic channel may be at least 2 nm. The width of the fluidic channel may be at least 3 nm. The width of the fluidic channel may be at least 4 nm. The width of the fluidic channel may be at least 5 nm. The width of the fluidic channel may be at least 6 nm. The width of the fluidic channel may be at least 7 nm. The width of the fluidic channel may be at least 8 nm. The width of the fluidic channel may be at least 9 nm. The width of the fluidic channel may be at least 10 nm.

The current sensor may comprise: (i) a current to voltage conversion circuit, (ii) a buffer, (iii) a sample and hold circuit, and (iv) an analog-to-digital (ADC) converter. The current sensor may be configured to detect a nucleoside, nucleotide, nucleoside pair, or nucleotide pair of only a single type. The current sensor may be configured to detect adenine. The current sensor may be configured to detect cytosine. The current sensor may be configured to detect guanine. The current sensor may be configured to detect thymine. The current sensor may be configured to detect adenine:thymine. The current sensor may be configured to detect cytosine:guanine. The current sensor may be configured to detect a methylated nucleoside, methylated nucleotide, methylated nucleoside pair, or methylated nucleotide pair of a single type. The current sensor may be configured to detect an amino acid of a single type. The current sensor may be configured to detect a sugar of a single type. The current sensor may comprise a plurality of current subsensors. Each sub-sensor of the plurality may be configured to detect a nucleoside, nucleotide, nucleoside pair, or nucleotide pair of a single type. Each sub-sensor of the plurality may be configured to detect a methylated nucleoside, methylated nucleotide, methylated nucleoside pair, or methylated nucleotide pair of a single type. Each sub-sensor of the plurality may be configured to detect an amino acid of a single type. Each sub-sensor of the plurality may be configured to detect a sugar of a single type.

The current sensor may be configured to detect nucleosides, nucleotides, nucleoside pairs, or nucleotide pairs of a plurality of types, which plurality is less than all types of nucleosides, nucleotides, nucleoside pairs, or nucleotide pairs. The current sensor may be configured to detect methylated nucleosides, methylated nucleotides, methylated nucleoside pairs, or methylated nucleotide pairs of a plurality of types, which plurality is less than all types of methylated nucleotides, methylated nucleoside pairs, or methylated nucleotide pairs. The current sensor may be configured to detect amino acids of a plurality of types, which plurality is less than all types of amino acids. The current sensor may be configured to detect sugars of a plurality of types, which plurality is less than all types of sugars.

The system may further comprise a positive electrophoresis electrode located at a first position along a length of the channel and a negative electrophoresis electrode located at a second position along the length of the channel, the positive and negative electrophoresis electrodes configured to advance the sample along all or a part of the length of the channel by electrophoresis.

The current sensor may comprise: (i) a current to voltage conversion circuit, (ii) a buffer, (iii) a sample and hold circuit, and (iv) an analog-to-digital (ADC) converter. The current sensor may be configured to detect a nucleoside, nucleotide, nucleoside pair, or nucleotide pair of only a single type. The current sensor may be configured to detect adenine. The current sensor may be configured to detect cytosine. The current sensor may be configured to detect guanine. The current sensor may be configured to detect thymine. The current sensor may be configured to detect adenine:thymine. The current sensor may be configured to detect cytosine:guanine. The current sensor may be configured to detect a methylated nucleoside, methylated nucleotide, methylated nucleoside pair, or methylated nucleotide pair of a single type. The current sensor may be configured to detect an amino acid of a single type. The current sensor may be configured to detect a sugar of a single type. The current sensor may comprise a plurality of current subsensors. Each sub-sensor of the plurality may be configured to detect a nucleoside, nucleotide, nucleoside pair, or nucleotide pair of a single type. Each sub-sensor of the plurality may be configured to detect a methylated nucleoside, methylated nucleotide, methylated nucleoside pair, or methylated nucleotide pair of a single type. Each sub-sensor of the plurality may be configured to detect an amino acid of a single type. Each sub-sensor of the plurality may be configured to detect a sugar of a single type.

The current sensor may be configured to detect nucleosides, nucleotides, nucleoside pairs, or nucleotide pairs of a plurality of types, which plurality is less than all types of nucleosides, nucleotides, nucleoside pairs, or nucleotide pairs. The current sensor may be configured to detect methylated nucleosides, methylated nucleotides, methylated nucleoside pairs, or methylated nucleotide pairs of a plurality of types, which plurality is less than all types of methylated nucleotides, methylated nucleoside pairs, or methylated nucleotide pairs. The current sensor may be configured to detect amino acids of a plurality of types, which plurality is less than all types of amino acids. The current sensor may be configured to detect sugars of a plurality of types, which plurality is less than all types of sugars.

The system may further comprise a positive electrophoresis electrode located at a first position along a length of the channel and a negative electrophoresis electrode located at a second position along the length of the channel, the positive and negative electrophoresis electrodes configured to advance the sample along all or a part of the length of the channel by electrophoresis. The method may further comprise advancing the sample along all or a part of the length of the channel by electrophoresis.

The method may further comprise detecting a time-ordered plurality of electric currents over a plurality of points in time, each electric current of the plurality associated with a different point in time, wherein the time-ordered plurality of electric currents is indicative of a presence or absence of the at least one molecule or the portion of the at least one molecule at different points in time as the at least one molecule or the portion of the at least one molecule passes through the current sensor. The method may further comprise subjecting the time-ordered plurality of electric currents to a window search procedure to determine points in time at which the at least one molecule or the portion of the at least one molecule passed through the current sensor. The window search procedure may comprise detecting and comparing a first window of time-ordered electric currents to a second window of time-ordered electric currents, wherein a change in electric current between the first window and the second window is indicative of a movement of the at least one molecule or the portion of the at least one molecule into or out of the current sensor. The first and second windows may differ by a single point in time. The size of the first and second windows may correspond to a number of portions of the at least one molecule passing through the current sensor at any point in time. The method may further comprise comparing all possible windows differing by a single point in time.

The sample may be a polymer and the at least one molecule may be a monomer.

In another aspect, a method for molecular analysis may comprise: (a) directing a biopolymer between a plurality of electrodes disposed along a fluid flow path, (b) using said plurality of electrodes to detect signals indicative of resonant tunneling current from individual subunits of said biopolymer, and (c) using said signals detected in (b) to generate a sequence of said biopolymer. The biopolymer may be a nucleic acid molecule. The individual subunits may be selected from the group consisting of: a nucleoside, a nucleotide, a nucleoside pair, and a nucleotide pair. The biopolymer may be a protein. The individual subunits may be amino acid residues. The plurality of electrodes may comprise two electrodes disposed on opposite sides of said fluid flow path. The method may achieve an accuracy of at least 95%. Said accuracy may be at least 98%. Said accuracy may be at least 90% over at least 50 subunits of said biopolymer without resequencing said biopolymer. Said accuracy may be at least 90% over at least 100 subunits of said biopolymer without resequencing said biopolymer.

In another aspect, a method for molecular analysis may comprise non-optically and directly detecting individual subunits of a biopolymer to generate a sequence of said biopolymer at an accuracy of at least 90% over at least 10 subunits without resequencing. The biopolymer may be a nucleic acid molecule. The individual subunits may be selected from the group consisting of: a nucleoside, a nucleotide, a nucleoside pair, and a nucleotide pair. The biopolymer may be a protein. The individual subunits may be amino acid residues. The detecting may comprise detecting resonant tunneling current from said individual subunits.

In another aspect, a system for molecular analysis may comprise: a plurality of electrodes disposed along a fluid flow path; and a controller operatively coupled to said plurality of electrodes, wherein said controller is configured to (i) subject a biopolymer to flow along said fluid flow path and between said plurality of electrodes, (ii) use said plurality of electrodes to detect signals indicative of resonant tunneling currents from individual subunits of said biopolymer, and (iii) use said signals detected in (ii) to generate a sequence of said biopolymer. Said plurality of electrodes may comprise two electrodes on opposite sides of said fluid flow path. Said plurality of electrodes may comprise a plurality of electrode sets, wherein a given electrode set of said plurality of electrode sets is configured to detect a given type of subunit of said biopolymer, which given type of subunit is different from other types of subunits of said biopolymer.

In another aspect, a system for molecule analysis may comprise a controller that is configured to non-optically and directly detect individual subunits of a biopolymer to generate a sequence of said biopolymer at an accuracy of at least 90% over at least 10 subunits of said biopolymer without resequencing said biopolymer. Said accuracy may be at least 95%. Said accuracy may be at least 98%. Said accuracy may be at least 90% over at least 50 submits of said biopolymer without resequencing said biopolymer. Said accuracy may be at least 90% over at least 100 submits of said biopolymer without resequencing said biopolymer.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 4A schematically illustrates a nucleotide to which the electron source is not tuned passing between the first and second electrodes.

FIG. 4B schematically illustrates the electric current detected by the current sensor when a nucleotide to which the electron source is not tuned passes between the first and second electrodes.

FIG. 16 shows a method for molecular analysis using non-optical detection.

DETAILED DESCRIPTION

Figure 1:
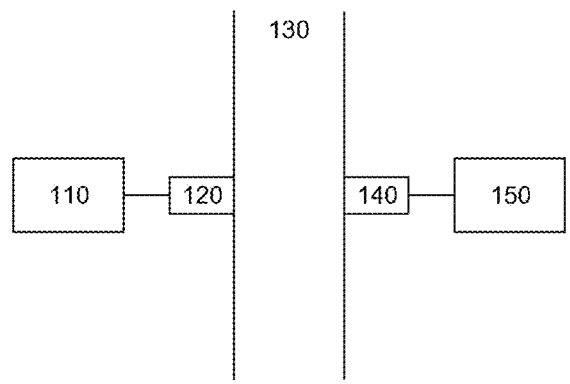
FIG. 1 schematically illustrates a system for molecular analysis comprising an electron source, a first electrode, a fluidic channel, a second electrode, and an electric current sensor.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Where values are described as ranges, it will be understood that such disclosure includes the disclosure of all possible sub-ranges within such ranges, as well as specific numerical values that fall within such ranges irrespective of whether a specific numerical value or specific sub-range is expressly stated.

As used herein, like characters refer to like elements.

The term "subject," as used herein, generally refers to an animal, such as a mammalian species (e.g., human) or avian (e.g., bird) species, or other organism, such as a plant. The subject can be a vertebrate, a mammal, a mouse, a primate, a simian or a human. Animals may include, but are not limited to, farm animals, sport animals, and pets. A subject can be a healthy or asymptomatic individual, an individual that has or is suspected of having a disease (e.g., cancer) or a pre-disposition to the disease, or an individual that is in need of therapy or suspected of needing therapy. A subject can be a patient.

The term "sample," as used herein, generally refers to a biological sample of a subject. The sample may be a tissue sample, such as a biopsy, core biopsy, needle aspirate, or fine needle aspirate. The sample may be a fluid sample, such as a blood sample, urine sample, or saliva sample. The sample may be a skin sample. The sample may be a cheek swab. The sample may be a plasma or serum sample. The sample may be a cell-free or cell free sample or a prepared sample (such as nucleic acid fragments). A cell-free sample may include extracellular polynucleotides. Extracellular polynucleotides may be isolated from a bodily sample that may be selected from a group consisting of blood, plasma, serum, urine, saliva, mucosal excretions, sputum, stool and tears.

The term "sequencing", as used herein, generally refers to methods and technologies for determining the sequence of molecular constituents of a macromolecule. The term "sequencing" may refer to nucleic acid sequencing, as defined herein. The term "sequencing" may refer to protein sequencing, polypeptide sequencing, or peptide sequencing, as defined herein.

The term "nucleic acid sequencing," as used herein, generally refers to methods and technologies for determining the sequence of nucleotide bases in one or more polynucleotides. The polynucleotides can be, for example, deoxyribonucleic acid (DNA) or ribonucleic acid (RNA), including variants or derivatives thereof (e.g., single stranded DNA or double stranded DNA). Nucleic acid sequencing can be performed by the systems and methods described herein. Such systems and methods may provide a plurality of raw genetic data corresponding to the genetic information of a subject (e.g., human), as generated by the device from a sample provided by the subject. In some cases, the systems and methods described herein may be used to sequence a nucleic acid that has been partially or fully methylated. In some cases, the systems and methods described herein may be used to determine a degree of methylation of a nucleic acid molecule.

The terms "protein sequencing," "polypeptide sequencing," and "peptide sequencing," as used herein, generally refers to methods and technologies for determining the sequence of amino acid residues in one or more proteins, polypeptides, or peptides. Protein sequencing, polypeptide sequencing, or peptide sequencing can be performed by the systems and methods described herein. Such systems and methods may provide a plurality of raw proteomic data corresponding to the proteomic information of a subject (e.g., human), as generated by the device from a sample provided by the subject.

FIG. 1 schematically illustrates a system for molecular analysis 100. The system may comprise an electron source 110, a first electrode 120, a fluidic channel (or fluid flow path) 130, a second electrode 140, and an electric current sensor 150. The electron source 110 may be electrically coupled to the first electrode 120, such as by a wire or other electric contact. The second electrode 140 may be electrically coupled to the electric current sensor 150, such as by a wire or other electric contact. The first and second electrodes may be physically separated by a gap. The gap may span all or a part of a width of the fluidic channel 130. The electron source may be distinct from the first electrode. The electron source may comprise the first electrode.

Figure 2:
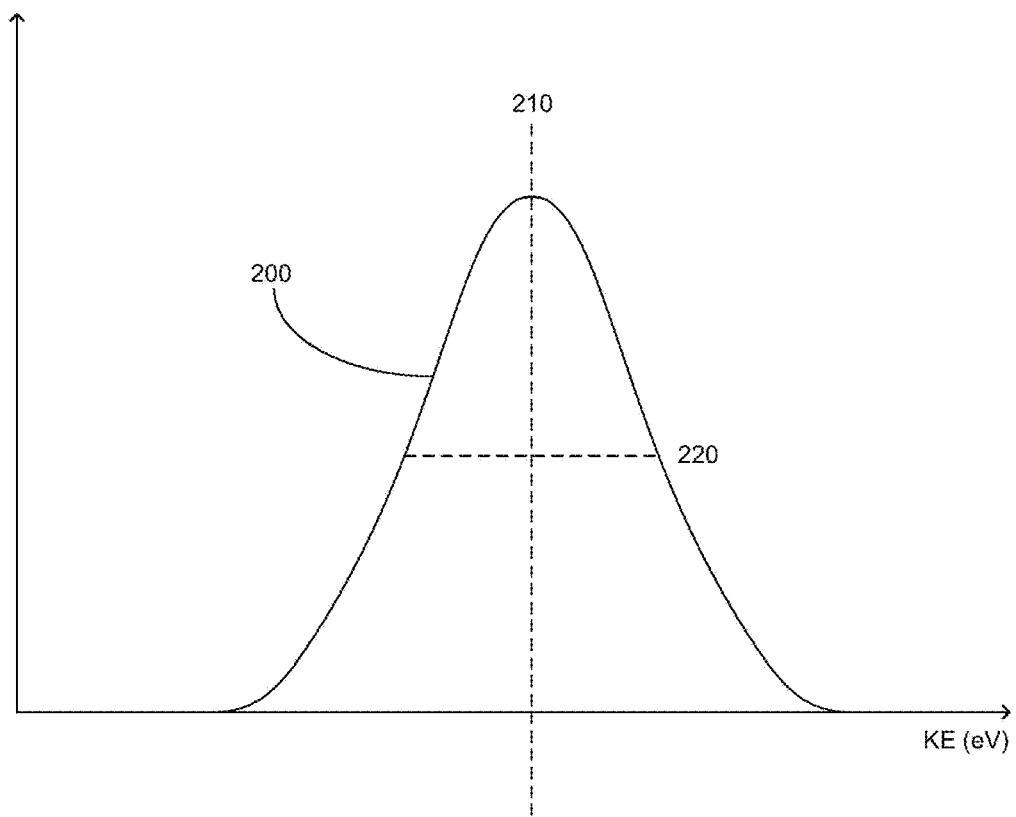
FIG. 2 depicts a distribution of electrons emitted by the electron source.

As shown in FIG. 2, the electron source 110 may be configured to emit a distribution of electrons 200 with a central kinetic energy 210 and a kinetic energy distribution. The kinetic energy distribution may emit electrons having a kinetic energy distribution that is narrower than the kinetic energy distribution of a thermal electron source (such as an electron source governed by the Maxwell-Boltzmann equations). For instance, the electrons may have a kinetic energy distribution having a full width at half maximum (FWHM) 220 that is less than the FWHM associated with a thermal electron source. The FWHM may be no greater than 1 electron Volt (eV), no greater than 0.5 eV, no greater than 0.1 eV, no greater than 0.05 eV, no greater than 0.01 eV, no greater than 0.005 eV, no greater than 1 meV, no greater than 0.5 meV, no greater than 0.1 meV, no greater than 0.05 meV, or no greater than 0.01 meV.

The electrons may have a central kinetic energy that is selected to excite an electronic transition of a particular nucleotide, nucleoside, nucleotide pair, nucleoside pair, methylated nucleotide, methylated nucleoside, methylated nucleotide pair, methylated nucleoside pair, or amino acid. For instance, the electrons may have a central kinetic energy that is selected to excite an electronic transition of adenine, cytosine, guanine, thymine, uracil, adenine:thymine, cytosine:guanine, or adenine:uracil. The electrons may have a central kinetic energy that is selected to excite an electronic transition of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, or valine. The electrons may have a central kinetic energy configured to excite a highest occupied molecular orbital (HOMO) to lowest unoccupied molecular orbital (LUMO) transition for a particular nucleotide, nucleoside, nucleotide pair, nucleoside pair, methylated nucleotide, methylated nucleoside, methylated nucleotide pair, methylated nucleoside pair, or amino acid. For instance, the electrons may have a central kinetic energy that is selected to excite a HOMO to LUMO transition of adenine, cytosine, guanine, thymine, uracil, adenine:thymine, cytosine:guanine, or adenine:uracil. The electrons may have a central kinetic energy that is selected to excite a HOMO to LUMO transition of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, or valine.

The electrons may have a central kinetic energy and a kinetic energy distribution that are selected so as to only excite an electronic transition of a particular nucleotide, nucleoside, nucleotide pair, nucleoside pair, methylated nucleotide, methylated nucleoside, methylated nucleotide pair, methylated nucleoside pair, or amino acid residue, while the electronic transitions of all other nucleotides, nucleosides, nucleotide pairs, nucleoside pairs, methylated nucleotides, methylated nucleosides, methylated nucleotide pairs, methylated nucleoside pairs, or amino acid residues are left unexcited. For instance, the electrons may have a central kinetic energy and a kinetic energy distribution that is selected to only excite adenine within a nucleic acid, while leaving all cytosine, guanine, thymine, and uracil in the nucleic acid unexcited.

The electrons may have a central kinetic energy and a kinetic energy distribution that is selected to excite any one of adenine, cytosine, guanine, thymine, or uracil within a nucleic acid, while leaving all other nucleosides or nucleotides in the nucleic acid unexcited. The electrons may have a central kinetic energy and a kinetic energy distribution that is selected to excite any of adenine:thymine, cytosine:guanine, or adenine:uracil within a nucleic acid, while leaving all other nucleoside pairs or nucleotide pairs in the nucleic acid unexcited. The electrons may have a central kinetic energy and a kinetic energy distribution that is selected to excite any of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, or valine within a protein, polypeptide, or peptide, while leaving all other amino acid residues in the protein, polypeptide, or peptide unexcited. The central kinetic energy required to excite a particular nucleotide, nucleoside, nucleotide pair, nucleoside pair, methylated nucleotide, methylated nucleoside, methylated nucleotide pair, methylated nucleoside pair, or amino acid may be determined experimentally. The central kinetic energy required to excite a particular nucleotide, nucleoside, nucleotide pair, nucleoside pair, methylated nucleotide, methylated nucleoside, methylated nucleotide pair, methylated nucleoside pair, or amino acid may be determined theoretically (for instance, using density functional theory calculations).

The electron source may comprise a thermal electron source and a quantum tunneling filter structure, as described herein.

Returning to the discussion of FIG. 1, the fluidic channel may be configured to receive a sample. The sample may be a liquid sample. The sample may comprise at least one molecule. For instance, the sample may comprise at least one nucleic acid, protein, polypeptide, or peptide molecule. The sample may be a polymer. The molecule may be a monomer. The sample may flow along a length of the channel past the gap between the first and second electrodes. The width of the fluidic channel may be at least 1 nm, at least 2 nm, at least 3 nm, at least 4 nm, at least 5 nm, or at least 10 nm.

The sample may be driven (or directed) through the channel by a variety of approaches. For instance, the sample may be driven by a pressure source, such as a pump and/or a compressor, or a plurality of pumps and/or compressors. In some situations, the sample may be driven by electrophoresis.

Figure 11:
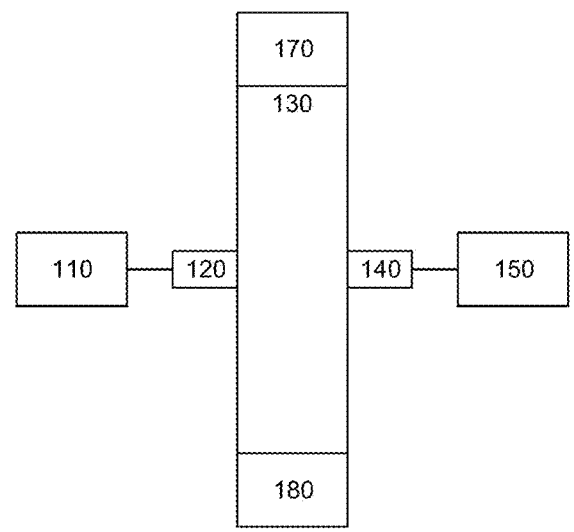
FIG. 11 schematically illustrates a system for molecular analysis in which a sample is driven by electrophoresis.

As shown in FIG. 11, the sample may be driven by electrophoresis. A system for molecular analysis 1100 may drive a sample by electrophoresis. The system may comprise any elements of any system described herein. For instance, the system may comprise the electron source 110, first electrode 120, fluidic channel 130, second electrode 140, and electric current sensor 150 of system 100 described herein. The system may further comprise a positive electrophoresis electrode 170 and a negative electrophoresis electrode 180. The positive electrophoresis electrode may be located at a first position along a length of the channel (such as at a first end of the channel or near a first end of the channel). The negative electrophoresis electrode may be located at a second position along the length of the channel (such as at a second end of the channel or near a second end of the channel). The positive and negative electrophoresis electrodes may be configured to advance the sample along all or a part of the length of the channel by electrophoresis.

Figure 12:
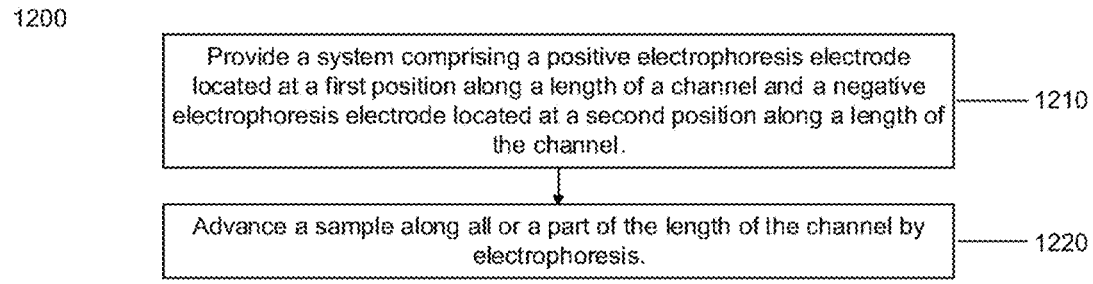
FIG. 12 shows a method for driving a molecule by electrophoresis.

FIG. 12 shows a method 1200 for driving a sample by electrophoresis. In a first operation 1210, the method may comprise providing a system comprising a positive electrophoresis electrode located at a first position along a length of a channel and a negative electrophoresis electrode located at a second position along a length of the channel. The positive and negative electrodes may be configured to advance a sample along all or part of a length of the channel by electrophoresis.

In a second operation, the method may comprise advancing the sample along all or a part of the length of the channel by electrophoresis.

The method 1200 may be implemented in combination with any other method described herein, such as any one or more of methods 1200, 1400, 1500, and 1600.

Returning to the discussion of FIG. 1, the first electrode may comprise a metal. For instance, the first electrode may comprise aluminum, copper, gold, silver, platinum, or titanium nitride (TiN). The second electrode may comprise a metal. For instance, the second electrode may comprise aluminum, copper, gold, silver, platinum, or TiN. The first electrode may be separated from the second electrode by a gap. The gap may be dimensioned to permit the sample to pass through the gap. The gap may be at least 1 nm, at least 2 nm, at least 3 nm, at least 4 nm, at least 5 nm, or at least 10 nm.

The electric current sensor may be configured to detect an electric current passing form the first electrode to the second electrode. When a molecule or portion of a molecule (such as a nucleotide, nucleoside, nucleotide pair, nucleoside pair, methylated nucleotide, methylated nucleoside, methylated nucleotide pair, methylated nucleoside pair, or amino acid residue) that is excited by the electron source passes through the gap, an electric current may flow from the first electrode to the second electrode. This electric current may be detected by the electric current sensor. The presence of a sustained electric current over a period of time may be indicative of the presence of the molecule or portion of the molecule within the gap during that time period. The electric current sensor may be electronically coupled to additional circuit elements. For instance, the electric current sensor may be a component of an integrated circuit.

The system 100 may be tunable, as described herein. For instance, the electron source may be tunable such that the central kinetic energy of the emitted electrons may be varied over time in order to induce different electronic transitions of different nucleotides, nucleosides, nucleotide pairs, nucleoside pairs, methylated nucleotides, methylated nucleosides, methylated nucleotide pairs, methylated nucleoside pairs, or amino acid residues at different points in time. For instance, the electron source may be tuned to induce electronic transitions in adenine at a first point in time, cytosine at a second point in time, guanine at a third point in time, thymine at a fourth point in time, and uracil at a fifth point in time. By rapidly varying the central kinetic energy (e.g. over a period of time shorter than the duration of time that a particular nucleotide or nucleoside in a nucleic acid resides in the gap) to correspond to the energies required to excite adenine, cytosine, guanine, thymine, and uracil, the identity of each nucleotide or nucleoside in a nucleic acid may be determined. The identity may be determined by noting which excitation (of adenine, cytosine, guanine, thymine, and uracil) gave rise to an appreciable electric current and which excitations did not. The electron source may be tuned to induce electronic transitions in adenine, cytosine, guanine, thymine, or uracil in any order.

The electron source may be tuned to induce electronic transitions in adenine:thymine at a first point in time, cytosine:guanine at a second point in time, and adenine:uracil at a third point in time. By rapidly varying the central kinetic energy (e.g. over a period of time shorter than the duration of time that a particular nucleotide pair or nucleoside pair in a nucleic acid resides in the gap) to correspond to the energies required to excite adenine:thymine, cytosine:guanine, and adenine:uracil, the identity of each nucleotide pair or nucleoside pair in a nucleic acid may be determined. The identity may be determined by noting which excitation (of adenine:thymine, cytosine:guanine, and adenine: uracil) gave rise to an appreciable electric current and which excitations did not. The electron source may be tuned to induce electronic transitions in adenine:thymine, cytosine:guanine, or adenine:uracil in any order.

The electron source may be tuned to induce electronic transitions in alanine at a first point in time, arginine at a second point in time, asparagine at a third point in time, aspartic acid at a fourth point in time, cysteine at a fifth point in time, glutamine at a sixth point in time, glutamic acid at a seventh point in time, glycine at an eighth point in time, histidine at a ninth point in time, isoleucine at a tenth point in time, leucine at an eleventh point in time, lysine at a twelfth point in time, methionine at a thirteenth point in time, phenylalanine at a fourteenth point in time, proline at a fifteenth point in time, serine at a sixteenth point in time, threonine at an seventeenth point in time, tryptophan at a eighteenth point in time, tyrosine at a nineteenth point in time, and valine at a twentieth point in time. By rapidly varying the central kinetic energy (e.g. over a period of time shorter than the duration of time that a particular amino acid residue in a protein, polypeptide, or peptide resides in the gap) to correspond to the energies required to excite alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine, the identity of each amino acid residue in a protein, polypeptide, or peptide may be determined. The identity may be determined by noting which excitation (of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, or valine) gave rise to an appreciable electric current and which excitations did not. The electron source may be tuned to induce electronic transitions in alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, or valine in any order.

Alternatively or in combination, the sequence of the macromolecule may be determined by employing multiple electron sources, multiple first and second electrode pairs, multiple current sensors, or any combination of these elements. For instance, the system may employ five sets of electron sources, first and second electrode pairs, and current sensors, each tuned to a different one of adenine, cytosine, guanine, thymine, and uracil. In this manner, each set may continuously monitor for the presence of adenine, cytosine, guanine, thymine, or uracil.

The system may employ three sets of electron sources, first and second electrode pairs, and current sensors, each tuned to a different one of adenine:thymine, cytosine:guanine, and adenine:uracil. In this manner, each set may continuously monitor for the presence of adenine:thymine, cytosine:guanine, or adenine:uracil.

The system may employ twenty sets of electron sources, first and second electrode pairs, and current sensors, each tuned to a different one of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine. In this manner, each set may continuously monitor for the presence of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, or valine.

The system may employ 1, 2, 3, 4, 5, 6, 7, 8, 9, 10, 11, 12, 13, 14, 15, 16, 17, 18, 19, 20, or more than 20 electron sources, first and second electrode pairs, or current sensors.

The system 100 may further comprise a controller. The controller may be coupled to the electron source and the current sensor. The controller may be configured to (i) direct the electron source to emit the electrons to the first electrode and the gap upon flow of the sample through the gap, and (ii) use the current sensor to detect an electric current directed from the first electrode to the second electrode.

Figure 3A:
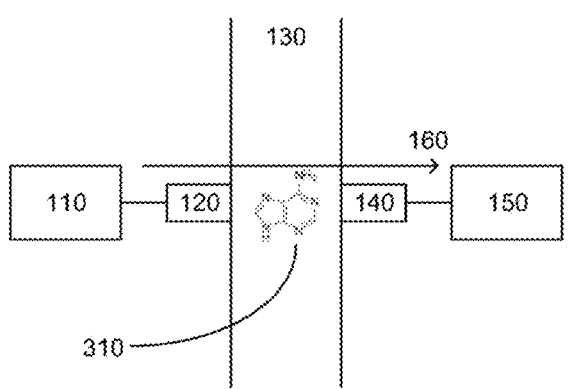
FIG. 3A schematically illustrates a nucleotide to which the electron source is tuned passing between the first and second electrodes.

FIG. 3A schematically illustrates a nucleotide to which the electron source is tuned passing between the first and second electrodes. For example, the electron source may be tuned to excite an electronic transition of adenine. Adenine 310 (for instance, an adenine nucleotide in single-stranded RNA or DNA) may pass through the gap between the first and second electrodes.

Figure 3B:
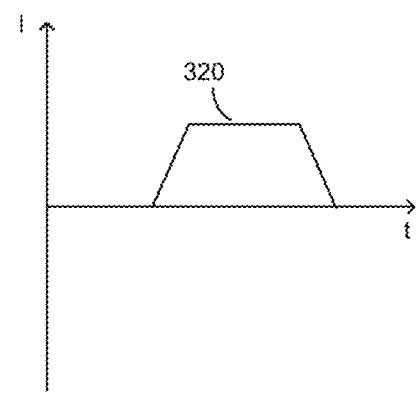
FIG. 3B schematically illustrates the electric current detected by the current sensor when a nucleotide to which the electron source is tuned passes between the first and second electrodes.

FIG. 3B schematically illustrates the electric current detected by the current sensor when a nucleotide to which the electron source is tuned passes between the first and second electrodes. When adenine passes between the first and second electrodes, electric current may be carried along adenine between the first and second electrodes, causing the electric current sensor to detect a current 320 for a period of time during which adenine is located between the first and second electrodes. The presence of adenine may be viewed as closing a switch between the first and second electrodes, allowing current to pass across the gap.

The value of the electric current passed by adenine may take a specific value. Values of the electric current passed by cytosine (when the electron source is tuned to a HOMO:LUMO transition of cytosine), guanine (when the electron source is tuned to a HOMO:LUMO transition of guanine), thymine (when the electron source is tuned to a HOMO:LUMO transition of thymine), and uracil (when the electron source is tuned to a HOMO:LUMO transition of uracil) may each take a different specific value than the value of the electric current passed by adenine (when the electron source is tuned to a HOMO:LUMO transition of adenine).

In general, the value of the electric current passed by a specific nucleotide, nucleoside, nucleotide pair, nucleoside pair, methylated nucleotide, methylated nucleoside, methylated nucleotide pair, methylated nucleoside pair, or amino acid residue may have a distinct value that is different from the value of the electric current passed by all other nucleotides, nucleosides, nucleotide pairs, nucleoside pairs, methylated nucleotides, methylated nucleosides, methylated nucleotide pairs, methylated nucleoside pairs, or amino acid residues. In this manner, the specific value of the current passed by a given nucleotide, nucleoside, nucleotide pair, nucleoside pair, methylated nucleotide, methylated nucleoside, methylated nucleotide pair, methylated nucleoside pair, or amino acid residue may also be indicative of the presence of that nucleotide, nucleoside, nucleotide pair, nucleoside pair, methylated nucleotide, methylated nucleoside, methylated nucleotide pair, methylated nucleoside pair, or amino acid residue.

FIG. 4A schematically illustrates a nucleotide to which the electron source is not tuned passing between the first and second electrodes. For example, the electron source may be tuned to excite an electronic transition of alanine. Cytosine 410 (for instance, a cytosine nucleotide in single-stranded RNA or DNA) may pass through the gap between the first and second electrodes.

FIG. 4B schematically illustrates the electric current detected by the current sensor when a nucleotide to which the electron source is not tuned passes between the first and second electrodes.

When cytosine passes between the first and second electrodes, no appreciable electric current may be carried along cytosine between the first and second electrodes, causing the electric current sensor to detect no appreciable current 420 for a period of time during which cytosine is located between the first and second electrodes. The presence of cytosine may be viewed as an open switch between the first and second electrodes, causing no appreciable current to pass across the gap.

Although FIGS. 3 and 4 are discussed with respect to adenine and cytosine, the detection principle holds for any nucleotide, nucleoside, nucleotide pair, nucleoside pair, methylated nucleotide, methylated nucleoside, methylated nucleotide pair, methylated nucleoside pair, or amino acid residue to which the electron source is tuned. That is, when the electron source is tuned to cytosine, guanine, thymine, or uracil, current will only be detected during the period of time in which that nucleotide or nucleoside is located between the first and second electrode; for all other nucleotides or nucleosides, no appreciable current will be detected.

When the electron source is tuned to adenine:thymine, cytosine:guanine, or adenine:uracil, current will only be detected during the period of time in which that nucleotide pair or nucleoside pair is located between the first and second electrode; for all other nucleotide pairs or nucleoside pairs, no appreciable current will be detected.

When the electron source is tuned to alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, or valine, current will only be detected during the period of time in which that amino acid residue is located between the first and second electrode; for all other amino acid residues, no appreciable current will be detected.

The electron source may comprise a thermal electron source and a quantum tunneling filter structure. The thermal electron source may produce a population of electrons having a thermal distribution of kinetic energies. The quantum tunneling filter structure may utilize a quantum tunneling phenomenon to filter the thermally distributed electrons. The quantum tunneling filter structure may be configured to transmit a majority of electrons having kinetic energies within a narrow range, while filtering a majority of electrons having kinetic energies outside of this range. Thus, the quantum tunneling filter structure may significantly narrow the electron kinetic energy distribution.

The quantum tunneling filter structure may comprise a quantum well.

Figure 5:
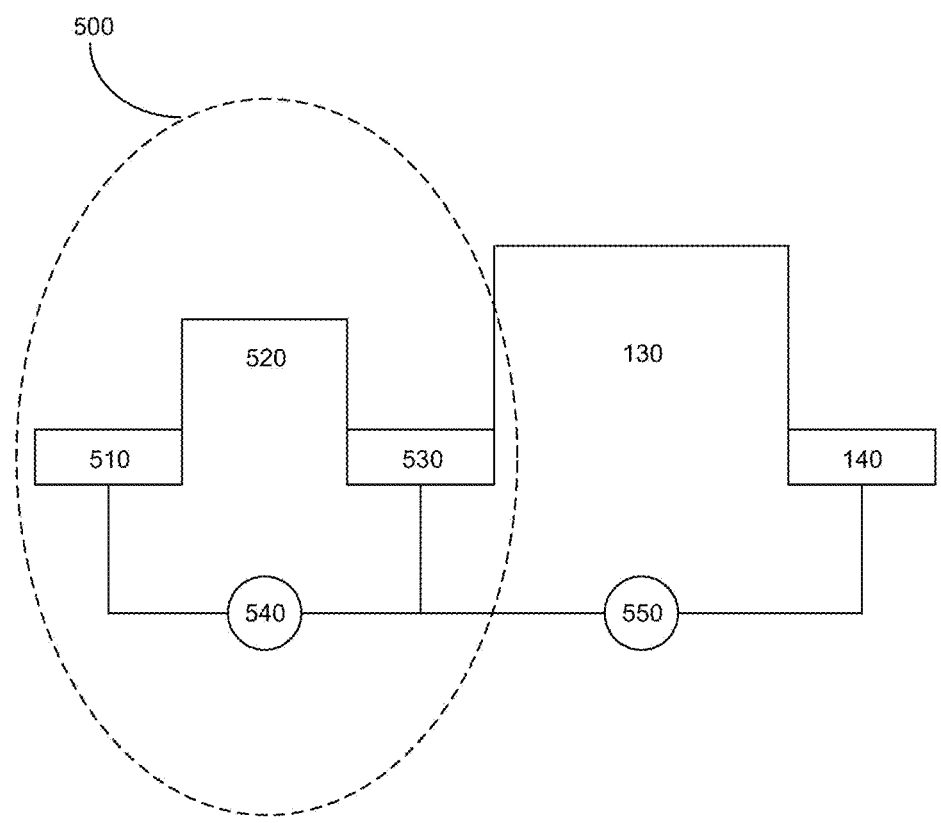
FIG. 5 schematically illustrates an energy band diagram for a system for molecular diagnosis utilizing a quantum well electron source.

FIG. 5 schematically illustrates an energy level diagram for a system for molecular diagnosis utilizing a quantum well electron source. The quantum well 500 may comprise a first conducting region 510 (also referred to as an emitter), an insulating region 520, and a second conducting region 530 (also referred to as a base). The first and second conducting regions may comprise metals. The first and second conducting regions may comprise metallic thin films, as described herein. The first and second conducting regions may comprise aluminum, copper, gold, silver, titanium nitride, or cobalt silicide. The insulating region may comprise a dielectric. The insulating region may comprise a dielectric thin film, as described herein. The insulating region may comprise a dielectric material, such as a silicon oxide ($SiO_x$), silicon dioxide ($SiO_2$), an aluminum oxide ($Al_xO_y$), aluminum (III) oxide ($Al_2O_3$), silicon nitride ($Si_3N_4$), or calcium fluoride (CaF). The second conducting region may function as the first electrode.

The quantum well may be configured such that electrons experience an increase in potential energy at the transition from the first conducting region to the insulating region and a decrease in potential energy at the transition from the insulating region to the second conducting region. The electrons may experience an increase in potential energy at the transition from the second conducting region to the channel and a decrease in potential energy at the transition from the channel to the second electrode. The quantum well structure may be biased by a quantum well bias voltage source 540. The channel may be biased by a channel bias voltage source 550.

Electrons may be filtered by the electron transmission properties of the quantum well. Electrons may only be transmitted to an appreciable extent if they have a kinetic energy which matches a resonance condition of the quantum well system. Thus, the electron distribution may be significantly narrowed by utilizing a quantum well as a kinetic energy filter.

When the quantum well bias and channel bias are set to a value of 0 V, the quantum well may filter all electrons other than those having a kinetic energy within a distribution that is determined by the material composition and thickness of the first conducting region, the material composition and thickness of the insulating region, and the material composition and thickness of the second conducting region. The transmission characteristics of the quantum well may thus be selected by careful selection of the compositions and thicknesses of the three layers of the quantum well. The compositions and thicknesses may be chosen to filter all electrons except those within a narrow distribution having a central kinetic energy that excites an electronic transition of a nucleotide, nucleoside, nucleotide pair, nucleoside pair, methylated nucleotide, methylated nucleoside, methylated nucleotide pair, methylated nucleoside pair, or amino acid. A system for molecular analysis may employ multiple quantum wells, with each quantum well having the compositions and thicknesses of the layers of the quantum well chosen such that each quantum well excites an electronic transition of a different nucleotide, nucleoside, nucleotide pair, nucleoside pair, methylated nucleotide, methylated nucleoside, methylated nucleotide pair, methylated nucleoside pair, or amino acid.

The transmission properties of the quantum well may be tuned by applying a non-zero quantum well bias and channel bias.

Figure 6:
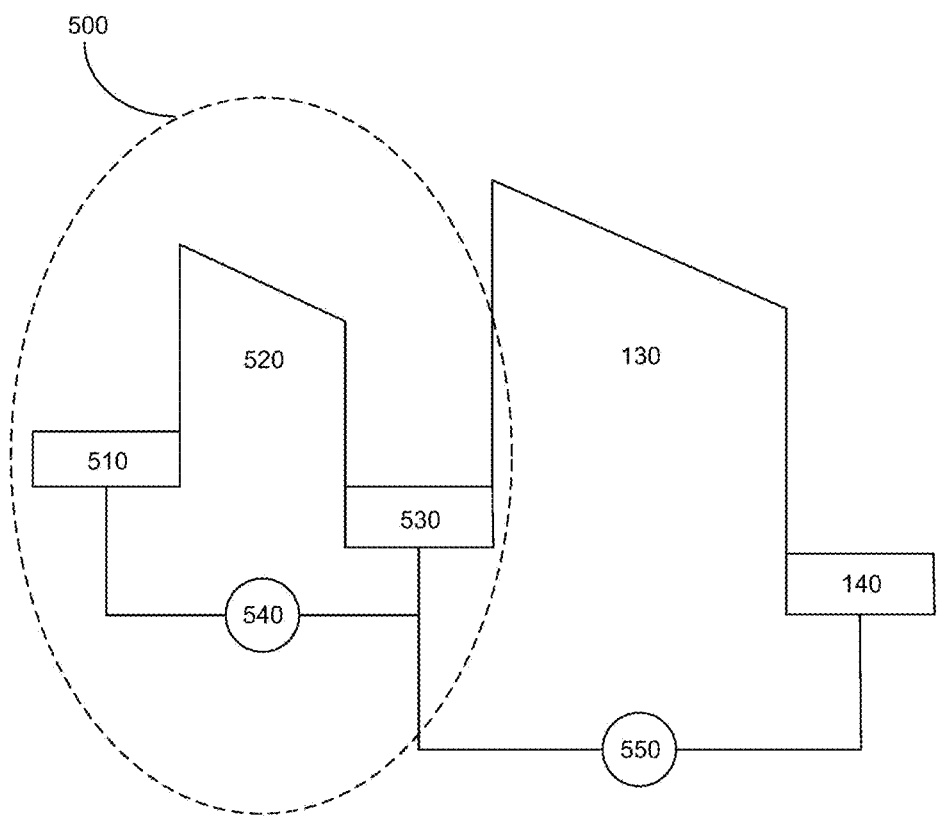
FIG. 6 schematically illustrates an energy level diagram for a system for molecular diagnosis utilizing a quantum well electron source with biasing potentials.

FIG. 6 schematically illustrates an energy level diagram for a system for molecular diagnosis utilizing a quantum well electron source with biasing potentials.

When the quantum well bias or channel bias are set to a non-zero value, the quantum well may filter all electrons other than those having a kinetic energy within a distribution that is determined not only by the material composition and thickness of the first conducting region, the material composition and thickness of the insulating region, and the material composition and thickness of the second conducting region, but also by the quantum well bias or channel bias values. The transmission characteristics of the quantum well may thus be selected less concern for the compositions and thicknesses of the three layers of the quantum well than in the case discussed with respect to FIG. 5. The quantum well bias or channel bias may be chosen to filter all electrons except those within a narrow distribution having a central kinetic energy that excites an electronic transition of a nucleotide, nucleoside, nucleotide pair, nucleoside pair, methylated nucleotide, methylated nucleoside, methylated nucleotide pair, methylated nucleoside pair, or amino acid. The quantum well bias or channel bias may be rapidly varied (for instance, within a time period less than 1 s, less than 100 ms, less than 10 ms, less than 1 ms, less than 100 µs, less than 10 µs, less than 1 µs, less than 100 nm, less than 10 ns, or less than 1 ns) to rapidly alter the electron central kinetic energy to excite particular nucleotides, nucleosides, nucleotide pairs, nucleoside pairs, methylated nucleotides, methylated nucleosides, methylated nucleotide pairs, methylated nucleoside pairs, or amino acids sequentially.

Figure 7:
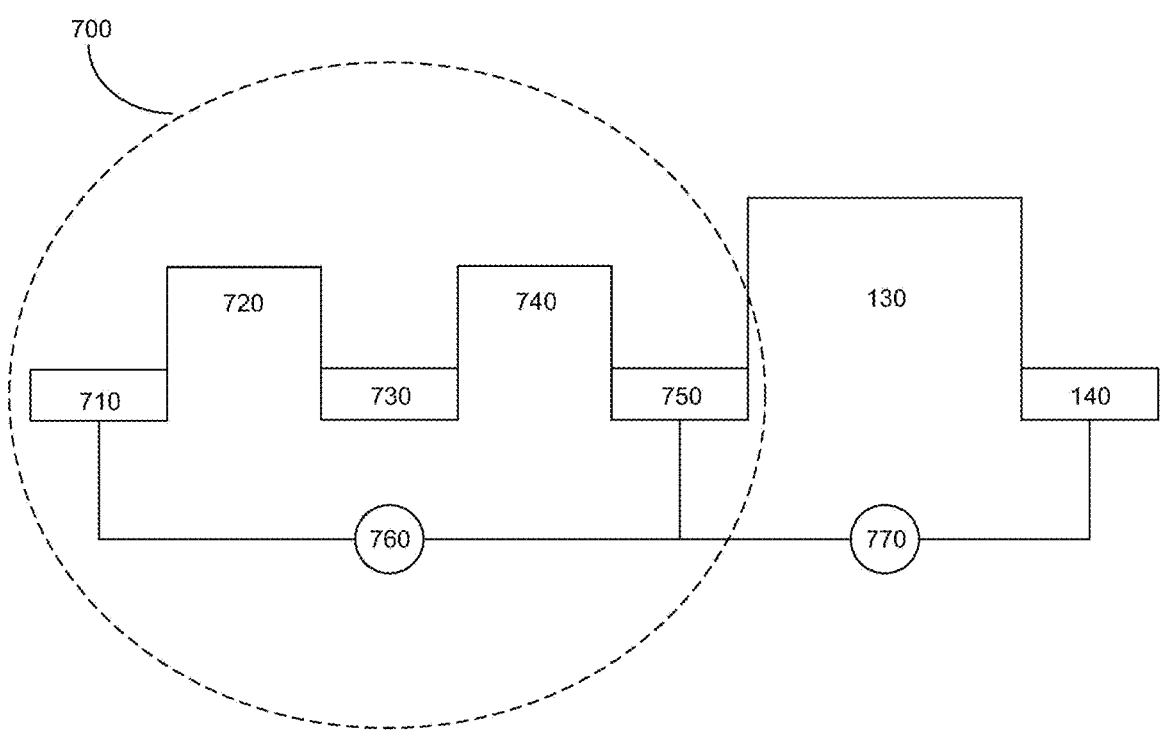
FIG. 7 schematically illustrates an energy level diagram for a system for molecular diagnosis utilizing a double quantum well electron source.

FIG. 7 schematically illustrates an energy level diagram for a system for molecular diagnosis utilizing a double quantum well electron source. The double quantum well 700 may comprise a first conducting region 710 (also referred to as an emitter), a first insulating region 720, a second conducting region 730, a second insulating region 740, and a third conducting region 750 (also referred to as a base). The first, second, and third conducting regions may comprise metals. The first, second, and third conducting regions may comprise metallic thin films, as described herein. The first, second, and third conducting regions may comprise aluminum, copper, gold, silver, titanium nitride, or cobalt silicide. The first and second insulating regions may comprise a dielectric. The first and second insulating regions may comprise a dielectric thin film, as described herein. The first and second insulating regions may comprise a dielectric material such as silicon oxide ($SiO_x$), silicon dioxide ($SiO_2$), an aluminum oxide ($Al_xO_y$), aluminum (III) oxide ($Al_2O_3$), silicon nitride ($Si_3N_4$), or calcium fluoride (CaF). The third conducting region may function as the first electrode.

The double quantum well may be configured such that electrons experience an increase in potential energy at the transition from the first conducting region to the first insulating region and a decrease in potential energy at the transition from the first insulating region to the second conducting region. The electrons may experience an increase in potential energy at the transition from the second conducting region to the second insulating region and a decrease in potential energy at the transition from the second insulating region to the third conducting region. The electrons may experience an increase in potential energy at the transition from the third conducting region to the channel and a decrease in potential energy at the transition from the channel to the second electrode. The double quantum well structure may be biased by a quantum well bias voltage source 760. The channel may be biased by a channel bias voltage source 770.

Electrons may be filtered by the electron transmission properties of the double quantum well. Electrons may only be transmitted to an appreciable extent if they have a kinetic energy which matches a resonance condition of the double quantum well system. Thus, the electron distribution may be significantly narrowed by utilizing a double quantum well as a kinetic energy filter. The electron distribution may be narrowed to a greater extent by a double quantum well structure than by the single quantum well structure described with respect to FIGS. 5 and 6. The double quantum well may be tuned in a similar manner as described with respect to the tuning of the single quantum well structure.

The quantum tunneling filter structure may comprise a higher-order quantum well. The quantum tunneling filter structure may comprise a triple quantum well comprising an alternating sequence of four conductive regions and three insulating regions. For instance, the triple quantum well may comprise a first conducting region (also referred to as an emitter), a first insulating region, a second conducting region, a second insulating region, a third conducting region, a third insulating region, and a fourth conducting region (also referred to as a base). The first, second, third, and fourth conducting regions may comprise metals. The first, second, third, and fourth conducting regions may comprise metallic thin films, as described herein. The first, second, third, and fourth conducting regions may comprise aluminum, copper, gold, silver, titanium nitride, or cobalt silicide. The first, second, and third insulating regions may comprise a dielectric. The first, second, and third insulating regions may comprise a dielectric thin film, as described herein. The first, second, and third insulating regions may comprise a dielectric materials such as silicon oxide ($SiO_x$), silicon dioxide ($SiO_2$), an aluminum oxide ($Al_xO_y$), aluminum (III) oxide ($Al_2O_3$), silicon nitride ($Si_3N_4$), or calcium fluoride (CaF). The fourth conducting region may function as the first electrode.

The quantum tunneling filter structure may comprise a quadruple quantum well comprising an alternating sequence of five conductive regions and four insulating regions. The quantum tunneling filter structure may comprise a quintuple quantum well comprising an alternating sequence of six conductive regions and five insulating regions. In general, the quantum tunneling filter structure may comprise any n-tuple quantum well, where n is a positive integer. An n-tuple quantum well may comprise an alternating sequence of n+1 conductive regions and n insulating regions, where again n is a positive integer. Higher-order quantum wells, with a relatively large value of n, may transmit narrower distributions of electrons than lower-order quantum wells, with a relatively small value of n. The (n+1)-th conducting region may function as the first electrode.

Figure 13A:
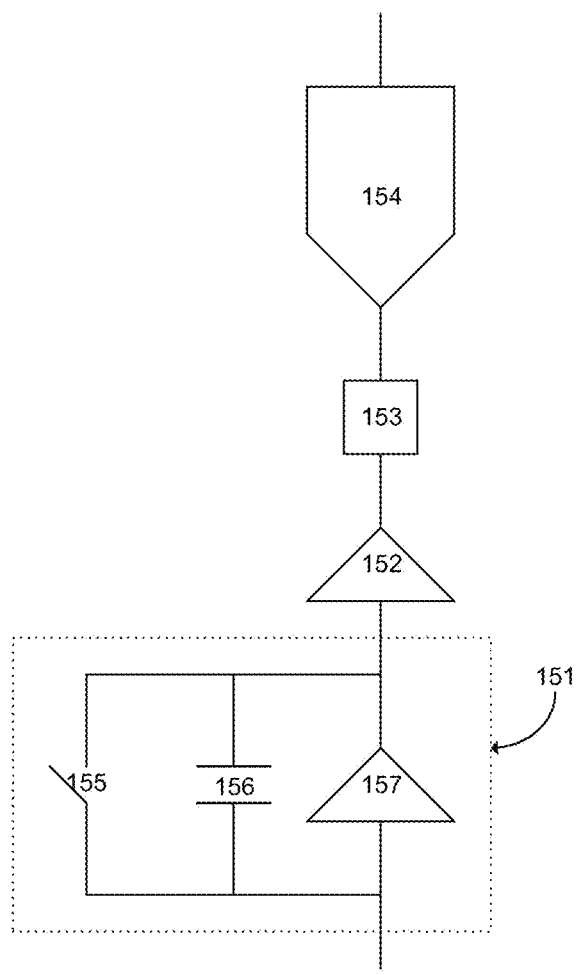
FIG. 13A schematically illustrates an electric current sensor configured to detect a presence of a molecule.

FIG. 13A schematically illustrates an electric current sensor 150 configured to detect a presence of a molecule.

The electric current sensor may comprise a current to voltage conversion circuit 151, a buffer 152, a sample and hold circuit 153, and an analog-to-digital converter (ADC) 154. The current to voltage conversion circuit may be electronically coupled to the buffer. The buffer may be electronically coupled to the sample and hold circuit. The sample and hold circuit may be electronically coupled to the ADC. The electric current sensor may be electronically coupled to the second electrode described herein.

The current to voltage conversion circuit may comprise a switch 155, a capacitor 156, and an operational amplifier 157. The switch may be configured to open at a specified time point as determined, for instance, by an electronic controller.

The operational amplifier may be configured in a negative feedback loop. The operational amplifier may be configured to hold a voltage of the second electrode or of a collector of a quantum filter at a desired electric potential. The desired electric potential may be selected such that electric current passes to the capacitor only when a particular electric current I associated with a particular molecule, such as a particular nucleotide, nucleoside, nucleotide pair, nucleoside pair, methylated nucleotide, methylated nucleoside, methylated nucleotide pair, methylated nucleoside pair, amino acid, or sugar, passes between the first and second electrodes described herein. A different particular electric current may be associated with different particular molecules. In this manner, the electric current may be indicative of the type of molecule being detected.

Upon opening of the switch, the capacitor may collect electric charge passing between the first and second electrodes. The capacitor may collect charge for a period of time T, resulting in a net charge $Q=I*T$. This may result in a voltage across the capacitor of $V=I*T/C$, where C is the capacitance of the capacitor. The period of time may be started and stopped by opening and closing the switch. The measured voltage may be sent to the sample and hold circuit and the ADC via the buffer. The ADC may output a digital code representing the capacitor voltage at different points in time.

This process may be repeated a number of times, such as at least 1, at least 2, at least 5, at least 10, at least 20, at least 50, at least 100, at least 200, at least 500, at least 1,000, at least 2,000, at least 5,000, at least 10,000, at least 20,000, at least 50,000, at least 100,000, at least 200,000, at least 500,000, or at least 1,000,000 times. In this manner, the sensor may output a digital signal indicating points in time at which a particular molecule is detected by the sensor.

In the event that the particular molecule to which the sensor is tuned is not present within an area of the channel to which the sensor is sensitive, a zero voltage signal (or a non-zero bias voltage) signal may be measured. In the event that the particular molecule to which the sensor is tuned is present within an area of the channel to which the sensor is sensitive, a signal greater than zero (or the bias voltage) may be measured. Thus, the presence or absence of the molecule at different points in time may be determined by noting the presence or absence of a signal greater than zero (or the bias voltage).

The sensor may be sensitive to an area within the channel that is physically larger than a single molecule. For instance, the sensor may be sensitive to an area within the channel that is as long as at least 1, at least 2, at least 5, at least 10, at least 20, at least 50, at least 100, at least 200, at least 500, or at least 1,000 molecules. Thus, more than 1 molecule to which the sensor is tuned may be present during any given time period. In such case, the sensor may give rise to a signal that is an integer multiple of the signal generated by a single molecule. For instance, if 1, 2, 5, 10, 20, 50, 100, 200, 500, or 1,000 molecules to which the sensor is tuned are present during a given period of time, the sensor may detect a signal that is 1, 2, 5, 10, 20, 50, 100, 200, 500, 1,000 times larger, respectively, than the signal detected during the presence of a single molecule. Thus, the number of molecules to which the sensor is tuned that are present at a given point in time may be determined by noting the strength of the detected signal.

The current sensor may be configured to detect only molecules of a single type. For instance, the current sensor may be configured to detect only monomers of a single type in a polymer. The current sensor may be configured to detect a nucleotide, nucleoside, nucleotide pair, or nucleoside pair of only a single type. For instance, the current sensor may be configured to detect only adenine, cytosine, guanine, thymine, or uracil. The current sensor may be configured to detect only adenine:thymine, adenine:uracil, or cytosine:guanine.

The current sensor may be configured to detect a methylated nucleotide, methylated nucleoside, methylated nucleotide pair, or methylated nucleoside pair of only a single type. For instance, the current sensor may be configured to detect only methylated adenine, methylated cytosine, methylated guanine, methylated thymine, or methylated uracil. The current sensor may be configured to detect only methylated adenine:thymine, methylated adenine:uracil, or methylated cytosine:guanine.

The current sensor may be configured to detect an amino acid of only a single type. For instance, the current sensor may be configured to detect only alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, or valine.

The current sensor may be configured to detect a sugar of only a single type.

The current sensor may comprise a plurality of current sub-sensors. For instance, the current sensor may comprise at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 50, at least 100, at least 200, at least 500, or at least 1,000 current sub-sensors. Each current sub-sensor may comprise an electronic circuit similar to the electronic circuit described herein with respect to FIG. 13A. For instance, each current sub-sensor may comprise a current to voltage conversion circuit, a buffer, a sample and hold circuit, and an ADC. The current to voltage conversion circuit may comprise a switch, a capacitor, and an operational amplifier.

Each current sub-sensor may be configured to detect only molecules of a single type. For instance, each current sub-sensor may be configured to detect only monomers of a single type in a polymer. Each current sub-sensor may be configured to detect a nucleotide, nucleoside, nucleotide pair, or nucleoside pair of only a single type. For instance, each current sub-sensor may be configured to detect only adenine, cytosine, guanine, thymine, or uracil. Each current sub-sensor may be configured to detect only adenine:thymine, adenine:uracil, or cytosine:guanine.

Each current sub-sensor may be configured to detect a methylated nucleotide, methylated nucleoside, methylated nucleotide pair, or methylated nucleoside pair of only a single type. For instance, each current sub-sensor may be configured to detect only methylated adenine, methylated cytosine, methylated guanine, methylated thymine, or methylated uracil. Each current sub-sensor may be configured to detect only methylated adenine:thymine, methylated adenine:uracil, or methylated cytosine:guanine.

Each current sub-sensor may be configured to detect an amino acid of only a single type. For instance, each current sub-sensor may be configured to detect only alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, or valine.

Each current sub-sensor may be configured to detect a sugar of only a single type.

Each current sub-sensor may be configured to detect a different type of molecule. For instance, the current sensor may comprise 4 current sub-sensors, with each of the current sub-sensors configured to detect one of adenine, cytosine, guanine, and thymine to sequence a DNA sequence or each of the current sub-sensors configured to detect one of adenine, cytosine, guanine, and uracil to sequence a RNA sequence. The current sensor may comprise 20 current sub-sensors, with each of the current sub-sensors configured to detect one of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine to sequence a protein.

Alternatively or in combination, at least 2, at least 5, at least 10, at least 20, at least 50, at least 100, at least 200, at least 500, or at least 1,000 current sub-sensors may be configured to detect the same type of molecule.

For instance, the current sensor may comprise 8 current sub-sensors, with two each of the current sub-sensors configured to detect one of adenine, cytosine, guanine, and thymine to sequence a DNA sequence or each of the current sub-sensors configured to detect one of adenine, cytosine, guanine, and uracil to sequence a RNA sequence. The current sensor may comprise 40 current sub-sensors, with two each of the current sub-sensors configured to detect one of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine to sequence a protein.

The current sensor may be configured to detect molecules of a plurality of types. For instance, the operational amplifier of the current sensor may be configured to sweep over a plurality of voltages of the second electrode or of a collector of a quantum filter. The plurality of voltages varied to correspond to different particular molecules, such as different particular nucleotides, nucleosides, nucleotide pairs, nucleoside pairs, methylated nucleotides, methylated nucleosides, methylated nucleotide pairs, methylated nucleoside pairs, amino acids, or sugars. The different molecules may be differentiated by giving rise to different electric currents.

The current sensor may be configured to detect nucleotides, nucleosides, nucleotide pairs, or nucleoside pairs of a plurality of types. The plurality of types may be all types of nucleotides, nucleosides, nucleotide pairs, or nucleoside pairs. The plurality of types may be less than all types of nucleotides, nucleosides, nucleotide pairs, or nucleoside pairs. For instance, the plurality of types may be any 2, 3, or 4 of adenine, cytosine, guanine, and thymine. The plurality of types may be any 2, 3, or 4 of adenine, cytosine, guanine, and uracil. The plurality of types may be any 2 of adenine: thymine and cytosine:guanine. The plurality of types may be any 2 of adenine:uracil and cytosine:guanine.

Alternatively or in combination, the current sensor may be configured to detect methylated nucleotides, methylated nucleosides, methylated nucleotide pairs, or methylated nucleoside pairs of a plurality of types. The plurality of types may be all types of methylated nucleotides, methylated nucleosides, methylated nucleotide pairs, or methylated nucleoside pairs. The plurality of types may be less than all types of methylated nucleotides, methylated nucleosides, methylated nucleotide pairs, or methylated nucleoside pairs. For instance, the plurality of types may be any 2, 3, or 4 of methylated adenine, methylated cytosine, methylated guanine, and methylated thymine. The plurality of types may be any 2, 3, or 4 of methylated adenine, methylated cytosine, methylated guanine, and methylated uracil. The plurality of types may be any 2 of methylated adenine:thymine and methylated cytosine:guanine. The plurality of types may be any 2 of methylated adenine:uracil and methylated cytosine:guanine.

The current sensor may be configured to detect amino acids of a plurality of types. The plurality of types may be all types of amino acids. The plurality of types may be less than all types of amino acids. For instance, the plurality of types may be any 2, 3, 4, 5, 6, 7, 8, 9, 10, 11, 12, 13, 14, 15, 16, 17, 18, 19, or 20 of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine.

The current sensor may be configured to detect sugars of a plurality of types. The plurality of types may be all types of sugars. The plurality of types may be less than all types of sugars.

Figure 13B:
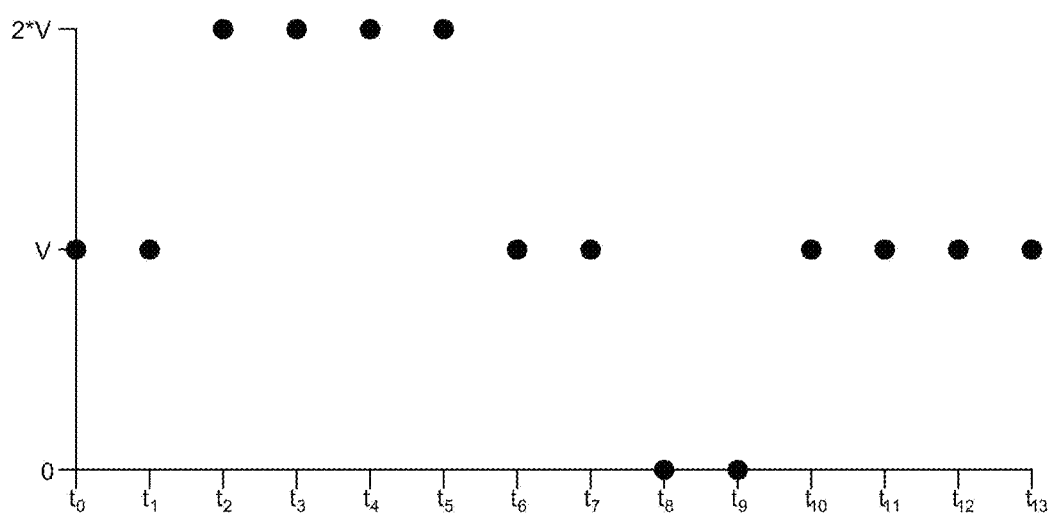
FIG. 13B schematically illustrates the electric current detected by the electric current sensor when a plurality of subunits of a sample pass along a channel between an electron source and an electrode coupled to the electric current sensor.

FIG. 13B schematically illustrates an exemplary electric current detected by the electric current sensor when a section of a nucleic acid passes along a channel between an electron source and an electrode coupled to the electric current sensor. In the example of FIG. 13B, the current sensor may be configured to detect cytosine only. In the example of FIG. 13B, the section of the nucleic acid may comprise the sequence ATTAGCACATGGTTGCAAA (with A representing adenine, C representing cytosine, G representing guanine, and T representing thymine). In the example of FIG. 13B, the sensor may be sensitive to an area of the channel spanning 6 nucleotides.

At an initial point in time $t_0$, the start of the sequence (ATTAGC) is within the area of the channel to which the current sensor is sensitive. Since a single C is present, the current sensor registers a voltage V at time $t_0$. At a next point in time $t_1$, the first A in the sequence has moved out of the area of the channel to which the current sensor is sensitive and the sequence TTAGCA is within the area of the channel to which the current sensor is sensitive. Since a single C is present, the current sensor registers a voltage V at time $t_1$. At a next point in time $t_2$, the sequence TAGCAC is within the area of the channel to which the current sensor is sensitive. Since two C's are present, the current sensor registers a voltage 2*V at time $t_2$. At a next point in time $t_3$, the sequence AGCACA is within the area of the channel to which the current sensor is sensitive. Since two C's are present, the current sensor registers a voltage 2*V at time $t_3$. At a next point in time $t_4$, the sequence GCACAT is within the area of the channel to which the current sensor is sensitive. Since two C's are present, the current sensor registers a voltage 2*V at time $t_4$. At a next point in time $t_5$, the sequence CACATG is within the area of the channel to which the current sensor is sensitive. Since two C's are present, the current sensor registers a voltage 2*V at time $t_5$. At a next point in time $t_6$, the sequence ACATGG is within the area of the channel to which the current sensor is sensitive. Since a single C is present, the current sensor registers a voltage V at time $t_6$. At a next point in time $t_7$, the sequence CATGCT is within the area of the channel to which the current sensor is sensitive. Since a single C is present, the current sensor registers a voltage V at time $t_7$. At a next point in time $t_8$, the sequence ATGGTT is within the area of the channel to which the current sensor is sensitive. Since no C is present, the current sensor registers of voltage 0 at time $t_8$. The time series for the exemplary sequence continues as indicated in FIG. 13B.

Figure 14A:
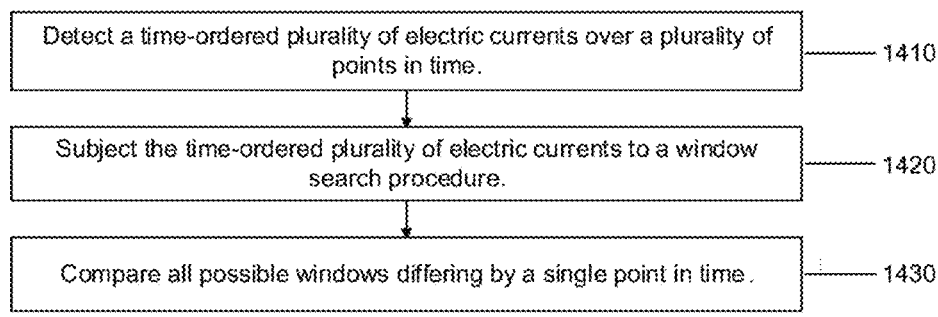
FIG. 14A shows a method for processing an electric current detected by an electric current sensor.

FIG. 14A shows a method for processing an electric current detected by an electric current sensor. In a first operation 1410, the method may comprise detecting a time-ordered plurality of electric currents over a plurality of points in time. The method may comprise detecting at least 1, at least 2, at least 5, at least 10, at least 20, at least 50, at least 100, at least 500, at least 1,000, at least 2,000, at least 5,000, at least 10,000, at least 20,000, at least 50,000, at least 100,000, at least 200,000, at least 500,000, or at least 1,000,000 time-ordered electric currents at a corresponding number of points in time. Each electric current may be associated with a different point in time.

The time-ordered plurality of electric currents may be indicative of a presence or absence of at least one molecule or portion of at least one molecule at different points in time. For instance, each of the electric currents may be indicative of the presence or absence of the molecule or the portion of the molecule, as described herein (for instance, with respect to FIG. 13A or 13B). Each of the electric currents may be indicative of the quantity of molecule or the portion of the molecule, as described herein (for instance, with respect to FIG. 13A or 13B). The time-ordered plurality of electric currents may be attained as the molecule or the portion of the molecule passes through a current sensor described herein.

In a second operation 1420, the method may comprise subjecting the time-ordered plurality of electric currents to a window search procedure to determine points in time at which the molecule or the portion of the molecule passed through the current sensor. The window search procedure may comprise comparing a first window of time-ordered electric currents to a second window of time-ordered electric currents.

The first and second windows may comprise any possible subset of the time-ordered electric currents. The first and second windows may comprise any possible ordered or sequential subset of the time-ordered electric currents. The first and second windows may have one or more elements in common. The first and second windows may differ in one or more elements. In some cases, the first and second windows may differ by a single element, which may correspond to a single point in time.

The first and second windows may be of any size. For instance, the first and second windows may comprise at least 1, at least 2, at least 5, at least 10, at least 20, at least 50, at least 100, at least 200, at least 500, or at least 1,000 time-ordered electric currents. The first and second windows may be of equal size. The size of the first and second windows may correspond to the number of molecules or the number of portions of a molecule that pass through a current sensor at any given point in time. For instance, if a current sensor is sensitive to 1, 2, 5, 10, 20, 50, 100, 200, 500, or 1,000 molecules at a time, the first and second windows may be 1, 2, 5, 10, 20, 50, 100, 200, 500, or 1,000 elements long, respectively.

Comparison of the time-ordered electric currents of the first and second windows may allow a determination of whether a molecule or portion of a molecule to which a sensor is sensitive moved into or out of a region to which the sensor is sensitive during a given moment in time. For instance, for first and second windows differing by a single point in time, the first element of the first window may be compared with the first element of the second window. If the second window starts at a later point in time than the first window, an increased current in the first element of the second window compared to the first element of the first window may indicate that a molecule or portion of a molecule has moved into the area to which the sensor is sensitive during the period of time that elapses between the start of the first window and the start of the second window. A current which does not change between the first element of the first window and the first element of the second window may indicate that the molecule or portion of the molecule has not moved into the area during such a time period.

Similarly, the last element of the first windows may be compared to the last element of the second window. If the second window starts at a later point in time than the first window, a decreased current in the last element of the second window compared to the last element of the first window may indicate that a molecule or portion of a molecule has moved out of the area to which the sensor is sensitive during the period of time that elapses between the end of the first window and the end of the second window. A current which does not change between the last element of the first window and the last element of the second window may indicate that the molecule or portion of the molecule has not moved out of the area during such a time period. In this manner, the current sensor may determine whether a single molecule or portion of a molecule has moved into or out of the area to which the current sensor is sensitive during a given period of time.

In a third operation 1430, the method may comprise comparing all possible windows differing by a single point in time. This comparison may yield a time series of indications as to whether or not the molecule or portion of the molecule moved into or out of the area to which the current sensor is sensitive.

The method may be applied to a polymer sample. The molecule may be a monomer of the polymer.

The method may be applied one or more of the sub-sensors described herein (for instance, with respect to FIGS. 13A and 13B) to obtain such time series of indications for every molecule or portion of a molecule of interest. For instance, the method may be applied to 4 time series of electric currents associated with 4 sub-sensors, with each sub-sensor configured to detect one of adenine, cytosine, guanine, and thymine. In such case, the method may yield 4 time series of indications as to whether each of adenine, cytosine, guanine, and thymine moved into or out of the area to which the sub-sensors are sensitive. The 4 time series of indications may be aligned to a common time axis to obtain a sequence of a nucleic acid.

Similarly, the method may be applied to 20 time series of electric currents associated with 20 sub-sensors, with each sub-sensor configured to detect one of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine. In such a case, the method may yield 20 times series of indications as to whether each of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine move into or out of the area to which the sub-sensors are sensitive. The 20 times series of indications may be aligned to a common time axis to obtain a sequence of a protein, peptide, or polypeptide.

Figure 14B:
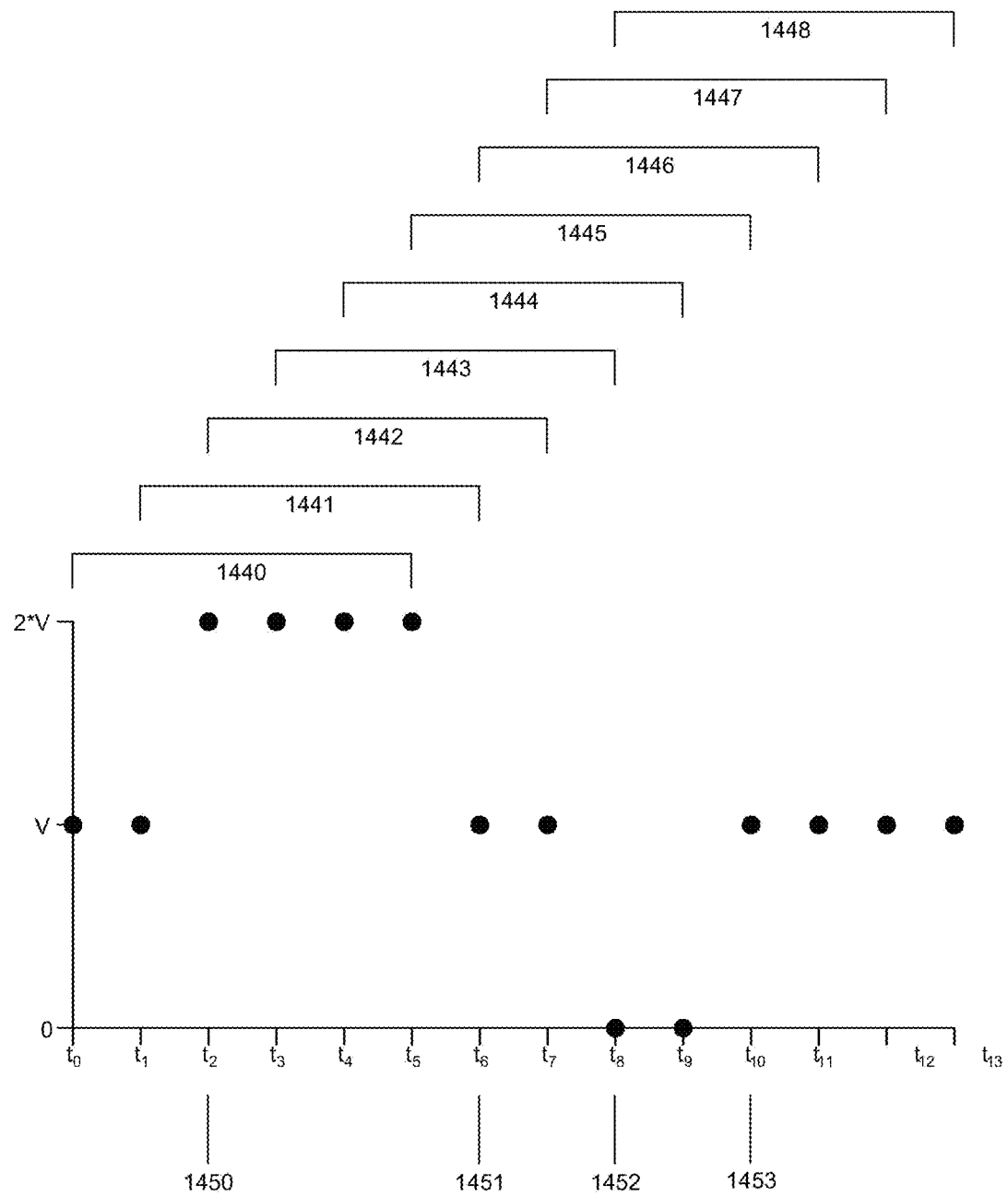
FIG. 14B shows an exemplary processed electric current.

FIG. 14B shows an exemplary processed electric current. In the example of FIG. 14B, the nucleic acid to be sequenced and the time-ordered electric current to be processed are identical to the nucleic acid and the time-ordered electric current (corresponding to a current sensor that is configured to detect cytosine), respectively, from FIG. 13B.

Figure 9:
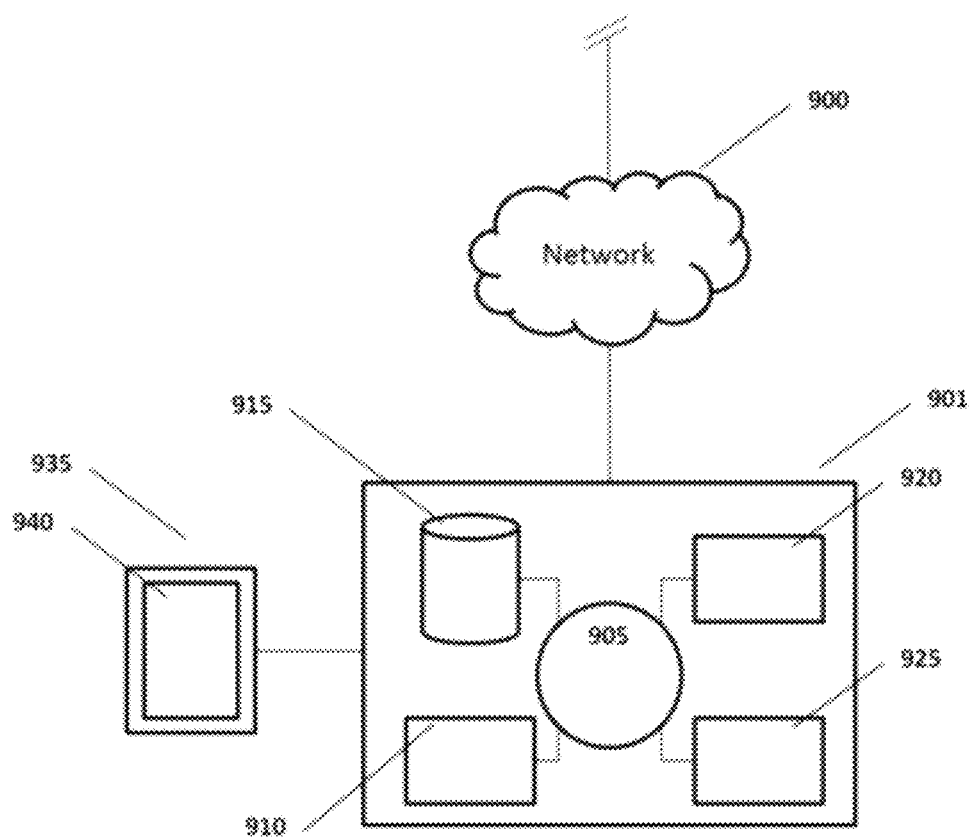
FIG. 9 shows an exemplary digital processing device programmed or otherwise configured to operate a system for molecular analysis.

As shown in FIG. 14B, 9 windows of 6 time points (corresponding to the number of nucleotides which may be in the area to which the current sensor is sensitive in the example of FIG. 13B) are possible. FIG. 14B depicts first, second, third, fourth, fifth, sixth, seventh, eighth, and ninth time windows 1440, 1441, 1442, 1443, 1444, 1445, 1446, 1447, and 1448, respectively. As depicted in FIG. 14B, the first and second, second and third, third and fourth, fourth and fifth, fifth and sixth, sixth and seventh, seventh and eighth, and eighth and ninth time windows each differ by a single point in time. Comparing the first elements of the second and third windows indicates a first time point 1450 at which a cytosine passed into the area to which the current sensor is sensitive. Comparing the first elements of the sixth and seventh windows indicates a first time point 1451 at which a cytosine passed out of the area to which the current sensor is sensitive. Comparing the first elements of the eighth and ninth windows indicates a second time point 1452 at which a cytosine passed out of the area to which the current sensor is sensitive.

Similarly, comparing the last elements of the first and second windows indicates the first time point 1451 at which a cytosine passed out of the area to which the current sensor is sensitive. Comparing the last elements of the third and fourth windows indicates the second time point 1452 at which the cytosine passed out of the area to which the current sensor is sensitive. Comparing the last elements of the fifth and sixth windows indicates a second time point 1453 at which a cytosine passed into the area to which the current sensor is sensitive.

Thus, it can be seen that comparison of the first elements of two windows and comparison of the last elements of two windows yields complementary information, forming a time record of when a particular molecule has passed into or out of the area to which a current sensor configured to detect that particular molecule. This information may be combined with similar information derived from other current sensors (such as current sub-sensors that are configured to detect other molecules as described herein) to yield a complete time record of molecules passing through a channel described herein. For instance, additional sub-sensors that are sensitive to adenine, guanine, and thymine may record time records of when adenine, guanine, and thymine pass into or out of the sensitive areas of their respective current sub-sensors. The time records for adenine, cytosine, guanine, and thymine may be aligned and combined to yield a complete sequence of a nucleic acid.

Similarly, time records for various amino acids, such as alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine, may be aligned and combined to yield a complete sequence of a protein, peptide, or polypeptide.

The systems for molecular analysis described herein may be fabricated using microfabrication or nanofabrication manufacturing techniques, such as one or more of solvent cleaning, Piranha cleaning, RCA cleaning, ion implantation, ultraviolet photolithography, deep ultraviolet photolithography, extreme ultraviolet photolithography, electron beam lithography, nanoimprint lithography, wet chemical etching, dry chemical etching, plasma etching, reactive ion etching, deep reactive ion etching, electron beam milling, thermal annealing, thermal oxidation, thin film deposition, chemical vapor deposition, molecular organic chemical deposition, low pressure chemical vapor deposition, plasma enhanced chemical vapor deposition, physical vapor deposition, sputtering, atomic layer deposition, molecular beam epitaxy, electrochemical deposition, wafer bonding, wire bonding, flip chip bonding, thermosonic bonding, wafer dicing, or any other microfabrication or nanofabrication manufacturing technique.

Figure 17A:
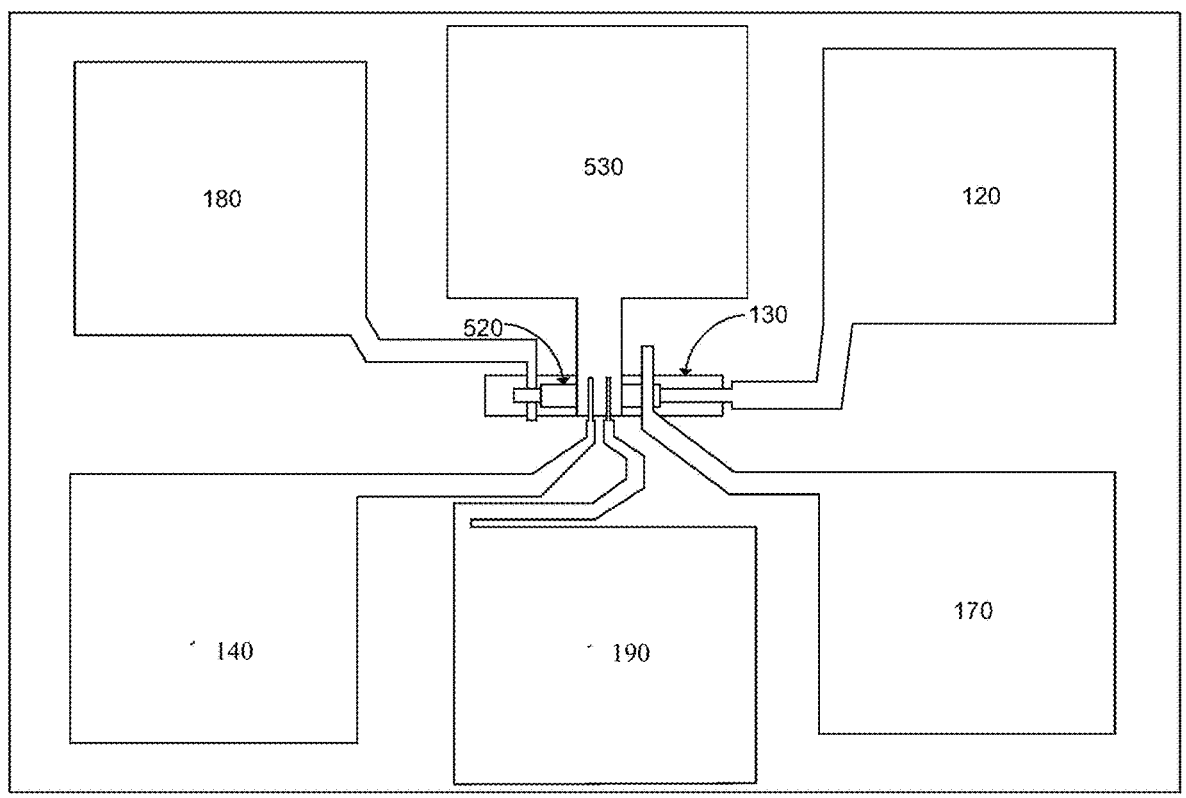
FIG. 17A shows a first example of a circuit architecture for a system for molecular analysis.

For instance, the systems for molecular analysis described herein (such as the system for molecular analysis described herein with respect to FIG. 17A) may be fabricated using any one or more of the following operations.

In a first operation, a substrate (such as a silicon wafer) may be subjected to an oxide growth process to form an oxide layer (such as a silicon dioxide layer) on the substrate. The oxide growth process may be a thermal oxide growth process. The oxide growth process may be a thin film deposition, chemical vapor deposition, molecular organic chemical deposition, low pressure chemical vapor deposition, plasma enhanced chemical vapor deposition, physical vapor deposition, sputtering, atomic layer deposition, molecular beam epitaxy, or an electrochemical deposition oxide growth process. The oxide growth process may produce an oxide layer that is about equal to a desired bond pad thickness. The desired bond pad thickness may be about at least 1 nm, at least 2 nm, at least 3 nm, at least 4 nm, at least 5 nm, at least 6 nm, at least 7 nm, at least 8 nm, at least 9 nm, at least 10 nm, at least 20 nm, at least 30 nm, at least 40 nm, at least 50 nm, at least 60 nm, at least 70 nm, at least 80 nm, at least 90 nm, at least 100 nm, at least 200 nm, at least 300 nm, at least 400 nm, at least 500 nm, at least 600 nm, at least 700 nm, at least 800 nm, at least 900 nm, at least 1 µm, at least 2 µm, at least 3 µm, at least 4 µm, at least 5 µm, at least 6 µm, at least 7 µm, at least 8 µm, at least 9 µm, at least 10 µm, at least 20 µm, at least 30 µm, at least 40 µm, at least 50 µm, at least 60 µm, at least 70 µm, at least 80 µm, at least 90 µm, at least 100 µm, at least 200 µm, at least 300 µm, at least 400 µm, at least 500 µm, at least 600 µm, at least 700 µm, at least 800 µm, at least 900 µm, at least 1 mm, or more. The desired bond pad thickness may be about at most 1 mm, at most 900 µm, at most 800 µm, at most 700 µm, at most 600 µm, at most 500 µm, at most 400 µm, at most 300 µm, at most 200 µm, at most 100 µm, at most 90 µm, at most 80 µm, at most 70 µm, at most 60 µm, at most 50 µm, at most 40 µm, at most 30 µm, at most 20 µm, at most 10 µm, at most 9 µm, at most 8 µm, at most 7 µm, at most 6 µm, at most 5 µm, at most 4 µm, at most 3 µm, at most 2 µm, at most 1 µm, at most 900 nm, at most 800 nm, at most 700 nm, at most 600 nm, at most 500 nm, at most 400 nm, at most 300 nm, at most 200 nm, at most 100 nm, at most 90 nm, at most 80 nm, at most 70 nm, at most 60 nm, at most 50 nm, at most 40 nm, at most 30 nm, at most 20 nm, at most 10 nm, at most 9 nm, at most 8 nm, at most 7 nm, at most 6 nm, at most 5 nm, at most 4 nm, at most 3 nm, at most 2 nm, at most 1 nm, or less. The desired bond pad thickness may be within a range defined by any two of the preceding values.

In a second operation, the oxide layer may be subjected to photolithography and etching to create one or more etched regions in the oxide layer. The photolithography and etching may be used to create at least 1, at least 2, at least 3, at least 4, at least 5, at least 6, at least 7, at least 8, at least 9, at least 10, or more etched regions. The etched regions may serve as regions that define the geometrical constraints of, for instance, the first electrode 120, second electrode 140, positive electrophoresis electrode 170, negative electrophoresis electrode 180, shield 190, and base 530 of FIG. 17A described herein. The one or more etched regions in the oxide layer may have a depth that is about equal to any desired bond pad thickness described herein.

In a third operation, the oxide layer may be subjected to a metal deposition process to create one or more metallic bond pads. The metal deposition process may be used to create at least 1, at least 2, at least 3, at least 4, at least 5, at least 6, at least 7, at least 8, at least 9, at least 10, or more bond pads. The one or more bond pads may correspond, for instance, to all or a portion of the first electrode 120, second electrode 140, positive electrophoresis electrode 170, negative electrophoresis electrode 180, shield 190, and base 530 of FIG. 17A described herein. The bond pads may have a thickness that is about equal to any desired bond pad thickness described herein. Each bond pad may comprise a conductor. For instance, each bond pad may comprise a metal such as aluminum, copper, silver, gold, nickel, palladium, or platinum. Each bond pad may comprise titanium nitride. Each bond pad may be formed by a thin film deposition, chemical vapor deposition, molecular organic chemical deposition, low pressure chemical vapor deposition, plasma enhanced chemical vapor deposition, physical vapor deposition, sputtering, atomic layer deposition, molecular beam epitaxy, or an electrochemical deposition oxide growth process.

In a fourth operation, a quantum well insulating region may be deposited atop the first electrode. The quantum well insulating region may be an insulator. The quantum well insulating region may be an oxide (such as silicon dioxide). The quantum well insulator region may serve as one layer of a quantum well described herein. The quantum well insulating region may have a thickness of at least 0.1 nm, at least 0.2 nm, at least 0.3 nm, at least 0.4 nm, at least 0.5 nm, at least 0.6 nm, at least 0.7 nm, at least 0.8 nm, at least 0.9 nm, at least 1 nm, at least 2 nm, at least 3 nm, at least 4 nm, at least 5 nm, at least 6 nm, at least 7 nm, at least 8 nm, at least 9 nm, at least 10 nm, or more. The quantum well insulating region may have a thickness of at most 10 nm, at most 9 nm, at most 8 nm, at most 7 nm, at most 6 nm, at most 5 nm, at most 4 nm, at most 3 nm, at most 2 nm, at most 1 nm, at most 0.9 nm, at most 0.8 nm, at most 0.7 nm, at most 0.6 nm, at most 0.5 nm, at most 0.4 nm, at most 0.3 nm, at most 0.2 nm, at most 0.1 nm, or less. The quantum well insulating region may have a thickness that is within a range defined by any two of the preceding values. The quantum well insulating region may be formed by a thin film deposition, chemical vapor deposition, molecular organic chemical deposition, low pressure chemical vapor deposition, plasma enhanced chemical vapor deposition, physical vapor deposition, sputtering, atomic layer deposition, molecular beam epitaxy, or an electrochemical deposition oxide growth process.

In a fifth operation, a quantum well conducting region may be deposited atop the base and quantum well insulator. The quantum well conducting region may be a conductor. For instance, the quantum well conducting region may comprise a metal such as aluminum, copper, silver, gold, nickel, palladium, or platinum. The quantum well conducting region may comprise titanium nitride. The quantum well conducting region may form all or a part of a quantum well conducting region described herein. The quantum well conducting region may have a thickness of at least 0.1 nm, at least 0.2 nm, at least 0.3 nm, at least 0.4 nm, at least 0.5 nm, at least 0.6 nm, at least 0.7 nm, at least 0.8 nm, at least 0.9 nm, at least 1 nm, at least 2 nm, at least 3 nm, at least 4 nm, at least 5 nm, at least 6 nm, at least 7 nm, at least 8 nm, at least 9 nm, at least 10 nm, or more. The quantum well conducting region may have a thickness of at most 10 nm, at most 9 nm, at most 8 nm, at most 7 nm, at most 6 nm, at most 5 nm, at most 4 nm, at most 3 nm, at most 2 nm, at most 1 nm, at most 0.9 nm, at most 0.8 nm, at most 0.7 nm, at most 0.6 nm, at most 0.5 nm, at most 0.4 nm, at most 0.3 nm, at most 0.2 nm, at most 0.1 nm, or less. The quantum well conducting region may have a thickness that is within a range defined by any two of the preceding values. The quantum well conducting region may be formed by a thin film deposition, chemical vapor deposition, molecular organic chemical deposition, low pressure chemical vapor deposition, plasma enhanced chemical vapor deposition, physical vapor deposition, sputtering, atomic layer deposition, molecular beam epitaxy, or an electrochemical deposition oxide growth process.

In a sixth operation, conductors may be deposited atop first electrode, base, and positive electrophoresis electrode to create metal tracts having a height about equal to that of the quantum well conducting region. The metal tracts may have a geometry as described herein (for instance, with reference to FIG. 17A). The conductors may comprise a metal such as aluminum, copper, silver, gold, nickel, palladium, or platinum. The conductors may have a thickness of at least 0.1 nm, at least 0.2 nm, at least 0.3 nm, at least 0.4 nm, at least 0.5 nm, at least 0.6 nm, at least 0.7 nm, at least 0.8 nm, at least 0.9 nm, at least 1 nm, at least 2 nm, at least 3 nm, at least 4 nm, at least 5 nm, at least 6 nm, at least 7 nm, at least 8 nm, at least 9 nm, at least 10 nm, or more. The conductors may have a thickness of at most 10 nm, at most 9 nm, at most 8 nm, at most 7 nm, at most 6 nm, at most 5 nm, at most 4 nm, at most 3 nm, at most 2 nm, at most 1 nm, at most 0.9 nm, at most 0.8 nm, at most 0.7 nm, at most 0.6 nm, at most 0.5 nm, at most 0.4 nm, at most 0.3 nm, at most 0.2 nm, at most 0.1 nm, or less. The conductors may have a thickness that is within a range defined by any two of the preceding values. The conductors may be formed by a thin film deposition, chemical vapor deposition, molecular organic chemical deposition, low pressure chemical vapor deposition, plasma enhanced chemical vapor deposition, physical vapor deposition, sputtering, atomic layer deposition, molecular beam epitaxy, or an electrochemical deposition oxide growth process.

In a seventh operation, an insulator may be deposited to electrically insulate the deposited components. The insulator may be an oxide (such as silicon dioxide). The insulator may have a thickness of at least 0.1 nm, at least 0.2 nm, at least 0.3 nm, at least 0.4 nm, at least 0.5 nm, at least 0.6 nm, at least 0.7 nm, at least 0.8 nm, at least 0.9 nm, at least 1 nm, at least 2 nm, at least 3 nm, at least 4 nm, at least 5 nm, at least 6 nm, at least 7 nm, at least 8 nm, at least 9 nm, at least 10 nm, or more. The insulator may have a thickness of at most 10 nm, at most 9 nm, at most 8 nm, at most 7 nm, at most 6 nm, at most 5 nm, at most 4 nm, at most 3 nm, at most 2 nm, at most 1 nm, at most 0.9 nm, at most 0.8 nm, at most 0.7 nm, at most 0.6 nm, at most 0.5 nm, at most 0.4 nm, at most 0.3 nm, at most 0.2 nm, at most 0.1 nm, or less. The insulator may have a thickness that is within a range defined by any two of the preceding values. The insulator may be formed by a thin film deposition, chemical vapor deposition, molecular organic chemical deposition, low pressure chemical vapor deposition, plasma enhanced chemical vapor deposition, physical vapor deposition, sputtering, atomic layer deposition, molecular beam epitaxy, or an electrochemical deposition oxide growth process.

In an eighth operation, a carbon nanotube may be deposited atop the insulated deposited components. The carbon nanotube may be aligned and placed. The carbon nanotube may be deposited by a thin film deposition, chemical vapor deposition, molecular organic chemical deposition, low pressure chemical vapor deposition, plasma enhanced chemical vapor deposition, physical vapor deposition, sputtering, atomic layer deposition, molecular beam epitaxy, or an electrochemical deposition oxide growth process. The carbon nanotube may form a channel 130 described herein. The carbon nanotube may be aligned as depicted in FIG. 17A, for instance. The carbon nanotube may have a thickness of at least 0.1 nm, at least 0.2 nm, at least 0.3 nm, at least 0.4 nm, at least 0.5 nm, at least 0.6 nm, at least 0.7 nm, at least 0.8 nm, at least 0.9 nm, at least 1 nm, at least 2 nm, at least 3 nm, at least 4 nm, at least 5 nm, at least 6 nm, at least 7 nm, at least 8 nm, at least 9 nm, at least 10 nm, or more. The carbon nanotube may have a thickness of at most 10 nm, at most 9 nm, at most 8 nm, at most 7 nm, at most 6 nm, at most 5 nm, at most 4 nm, at most 3 nm, at most 2 nm, at most 1 nm, at most 0.9 nm, at most 0.8 nm, at most 0.7 nm, at most 0.6 nm, at most 0.5 nm, at most 0.4 nm, at most 0.3 nm, at most 0.2 nm, at most 0.1 nm, or less. The carbon nanotube may have a thickness that is within a range defined by any two of the preceding values.

In a ninth operation, conductors may be deposited atop first electrode, base, and positive and negative electrophoresis electrodes to create metal tracts having a height about equal to that of the carbon nanotube. The metal tracts may have a geometry as described herein (for instance, with reference to FIG. 17A). The conductors may comprise a metal such as aluminum, copper, silver, gold, nickel, palladium, or platinum. The conductors may have a thickness of at least 0.1 nm, at least 0.2 nm, at least 0.3 nm, at least 0.4 nm, at least 0.5 nm, at least 0.6 nm, at least 0.7 nm, at least 0.8 nm, at least 0.9 nm, at least 1 nm, at least 2 nm, at least 3 nm, at least 4 nm, at least 5 nm, at least 6 nm, at least 7 nm, at least 8 nm, at least 9 nm, at least 10 nm, or more. The conductors may have a thickness of at most 10 nm, at most 9 nm, at most 8 nm, at most 7 nm, at most 6 nm, at most 5 nm, at most 4 nm, at most 3 nm, at most 2 nm, at most 1 nm, at most 0.9 nm, at most 0.8 nm, at most 0.7 nm, at most 0.6 nm, at most 0.5 nm, at most 0.4 nm, at most 0.3 nm, at most 0.2 nm, at most 0.1 nm, or less. The conductors may have a thickness that is within a range defined by any two of the preceding values. The conductors may be formed by a thin film deposition, chemical vapor deposition, molecular organic chemical deposition, low pressure chemical vapor deposition, plasma enhanced chemical vapor deposition, physical vapor deposition, sputtering, atomic layer deposition, molecular beam epitaxy, or an electrochemical deposition oxide growth process.

In a tenth operation, an insulator may be deposited to electrically insulate the deposited components. The insulator may be an oxide (such as silicon dioxide). The insulator may have a thickness of at least 0.1 nm, at least 0.2 nm, at least 0.3 nm, at least 0.4 nm, at least 0.5 nm, at least 0.6 nm, at least 0.7 nm, at least 0.8 nm, at least 0.9 nm, at least 1 nm, at least 2 nm, at least 3 nm, at least 4 nm, at least 5 nm, at least 6 nm, at least 7 nm, at least 8 nm, at least 9 nm, at least 10 nm, or more. The insulator may have a thickness of at most 10 nm, at most 9 nm, at most 8 nm, at most 7 nm, at most 6 nm, at most 5 nm, at most 4 nm, at most 3 nm, at most 2 nm, at most 1 nm, at most 0.9 nm, at most 0.8 nm, at most 0.7 nm, at most 0.6 nm, at most 0.5 nm, at most 0.4 nm, at most 0.3 nm, at most 0.2 nm, at most 0.1 nm, or less. The insulator may have a thickness that is within a range defined by any two of the preceding values. The insulator may be formed by a thin film deposition, chemical vapor deposition, molecular organic chemical deposition, low pressure chemical vapor deposition, plasma enhanced chemical vapor deposition, physical vapor deposition, sputtering, atomic layer deposition, molecular beam epitaxy, or an electrochemical deposition oxide growth process.

In an eleventh operation, conductors may be deposited to create metal tracts that form the second electrode and shield described herein. The metal tracts may have a geometry as described herein (for instance, with reference to FIG. 17A). The conductors may comprise a metal such as aluminum, copper, silver, gold, nickel, palladium, or platinum. The conductors may have a thickness of at least 0.1 nm, at least 0.2 nm, at least 0.3 nm, at least 0.4 nm, at least 0.5 nm, at least 0.6 nm, at least 0.7 nm, at least 0.8 nm, at least 0.9 nm, at least 1 nm, at least 2 nm, at least 3 nm, at least 4 nm, at least 5 nm, at least 6 nm, at least 7 nm, at least 8 nm, at least 9 nm, at least 10 nm, at least 20 nm, at least 30 nm, at least 40 nm, at least 50 nm, at least 60 nm, at least 70 nm, at least 80 nm, at least 90 nm, at least 100 nm, or more. The conductors may have a thickness of at most 100 nm, at most 90 nm, at most 80 nm, at most 70 nm, at most 60 nm, at most 50 nm, at most 40 nm, at most 30 nm, at most 20 nm, at most 10 nm, at most 9 nm, at most 8 nm, at most 7 nm, at most 6 nm, at most 5 nm, at most 4 nm, at most 3 nm, at most 2 nm, at most 1 nm, at most 0.9 nm, at most 0.8 nm, at most 0.7 nm, at most 0.6 nm, at most 0.5 nm, at most 0.4 nm, at most 0.3 nm, at most 0.2 nm, at most 0.1 nm, or less. The conductors may have a thickness that is within a range defined by any two of the preceding values. The conductors may be formed by a thin film deposition, chemical vapor deposition, molecular organic chemical deposition, low pressure chemical vapor deposition, plasma enhanced chemical vapor deposition, physical vapor deposition, sputtering, atomic layer deposition, molecular beam epitaxy, or an electrochemical deposition oxide growth process.

In a twelfth operation, conductors may be deposited atop first electrode, base, and positive and negative electrophoresis electrodes to create metal tracts having a height about equal to that of the second electrode and shield. The metal tracts may have a geometry as described herein (for instance, with reference to FIG. 17A). The conductors may comprise a metal such as aluminum, copper, silver, gold, nickel, palladium, or platinum. The conductors may have a thickness of at least 0.1 nm, at least 0.2 nm, at least 0.3 nm, at least 0.4 nm, at least 0.5 nm, at least 0.6 nm, at least 0.7 nm, at least 0.8 nm, at least 0.9 nm, at least 1 nm, at least 2 nm, at least 3 nm, at least 4 nm, at least 5 nm, at least 6 nm, at least 7 nm, at least 8 nm, at least 9 nm, at least 10 nm, at least 20 nm, at least 30 nm, at least 40 nm, at least 50 nm, at least 60 nm, at least 70 nm, at least 80 nm, at least 90 nm, at least 100 nm, or more. The conductors may have a thickness of at most 100 nm, at most 90 nm, at most 80 nm, at most 70 nm, at most 60 nm, at most 50 nm, at most 40 nm, at most 30 nm, at most 20 nm, at most 10 nm, at most 9 nm, at most 8 nm, at most 7 nm, at most 6 nm, at most 5 nm, at most 4 nm, at most 3 nm, at most 2 nm, at most 1 nm, at most 0.9 nm, at most 0.8 nm, at most 0.7 nm, at most 0.6 nm, at most 0.5 nm, at most 0.4 nm, at most 0.3 nm, at most 0.2 nm, at most 0.1 nm, or less. The conductors may have a thickness that is within a range defined by any two of the preceding values. The conductors may be formed by a thin film deposition, chemical vapor deposition, molecular organic chemical deposition, low pressure chemical vapor deposition, plasma enhanced chemical vapor deposition, physical vapor deposition, sputtering, atomic layer deposition, molecular beam epitaxy, or an electrochemical deposition oxide growth process.

In a thirteenth operation, an insulator may be deposited to electrically insulate the deposited components. The insulator may be an oxide (such as silicon dioxide). The insulator may have a thickness of at least 0.1 nm, at least 0.2 nm, at least 0.3 nm, at least 0.4 nm, at least 0.5 nm, at least 0.6 nm, at least 0.7 nm, at least 0.8 nm, at least 0.9 nm, at least 1 nm, at least 2 nm, at least 3 nm, at least 4 nm, at least 5 nm, at least 6 nm, at least 7 nm, at least 8 nm, at least 9 nm, at least 10 nm, at least 20 nm, at least 30 nm, at least 40 nm, at least 50 nm, at least 60 n, at least 70 nm, at least 80 nm, at least 90 nm, at least 100 nm, or more. The insulator may have a thickness of at most 100 nm, at most 90 nm, at most 80 nm, at most 70 nm, at most 60 nm, at most 50 nm, at most 40 nm, at most 30 nm, at most 20 nm, at most 10 nm, at most 9 nm, at most 8 nm, at most 7 nm, at most 6 nm, at most 5 nm, at most 4 nm, at most 3 nm, at most 2 nm, at most 1 nm, at most 0.9 nm, at most 0.8 nm, at most 0.7 nm, at most 0.6 nm, at most 0.5 nm, at most 0.4 nm, at most 0.3 nm, at most 0.2 nm, at most 0.1 nm, or less. The insulator may have a thickness that is within a range defined by any two of the preceding values. The insulator may be formed by a thin film deposition, chemical vapor deposition, molecular organic chemical deposition, low pressure chemical vapor deposition, plasma enhanced chemical vapor deposition, physical vapor deposition, sputtering, atomic layer deposition, molecular beam epitaxy, or an electrochemical deposition oxide growth process.

In a fourteenth operation, conductors may be deposited atop first electrode, second electrode, shield, base, and positive and negative electrophoresis electrodes to create thick metal films. The metal tracts may have a geometry as described herein (for instance, with reference to FIG. 17A). The conductors may comprise a metal such as aluminum, copper, silver, gold, nickel, palladium, or platinum. The conductors may have a thickness of at least 1 nm, at least 2 nm, at least 3 nm, at least 4 nm, at least 5 nm, at least 6 nm, at least 7 nm, at least 8 nm, at least 9 nm, at least 10 nm, at least 20 nm, at least 30 nm, at least 40 nm, at least 50 nm, at least 60 nm, at least 70 nm, at least 80 nm, at least 90 nm, at least 100 nm, at least 200 nm, at least 300 nm, at least 400 nm, at least 500 nm, at least 600 nm, at least 700 nm, at least 800 nm, at least 900 nm, at least 1,000 nm, or more. The conductors may have a thickness of at most 1,000 nm, at most 900 nm, at most 800 nm, at most 700 nm, at most 600 nm, at most 500 nm, at most 400 nm, at most 300 nm, at most 200 nm, at most 100 nm, at most 90 nm, at most 80 nm, at most 70 nm, at most 60 nm, at most 50 nm, at most 40 nm, at most 30 nm, at most 20 nm, at most 10 nm, at most 9 nm, at most 8 nm, at most 7 nm, at most 6 nm, at most 5 nm, at most 4 nm, at most 3 nm, at most 2 nm, at most 1 nm, or less. The conductors may have a thickness that is within a range defined by any two of the preceding values. The conductors may be formed by a thin film deposition, chemical vapor deposition, molecular organic chemical deposition, low pressure chemical vapor deposition, plasma enhanced chemical vapor deposition, physical vapor deposition, sputtering, atomic layer deposition, molecular beam epitaxy, or an electrochemical deposition oxide growth process.

Any one or more of the first, second, third, fourth, fifth, sixth, seventh, eighth, ninth, tenth, eleventh, twelfth, thirteenth, and fourteenth operations may be combined, in any possible order, to produce a system for molecular analysis described herein (such as a system described herein with respect to FIG. 17A).

Figure 8:
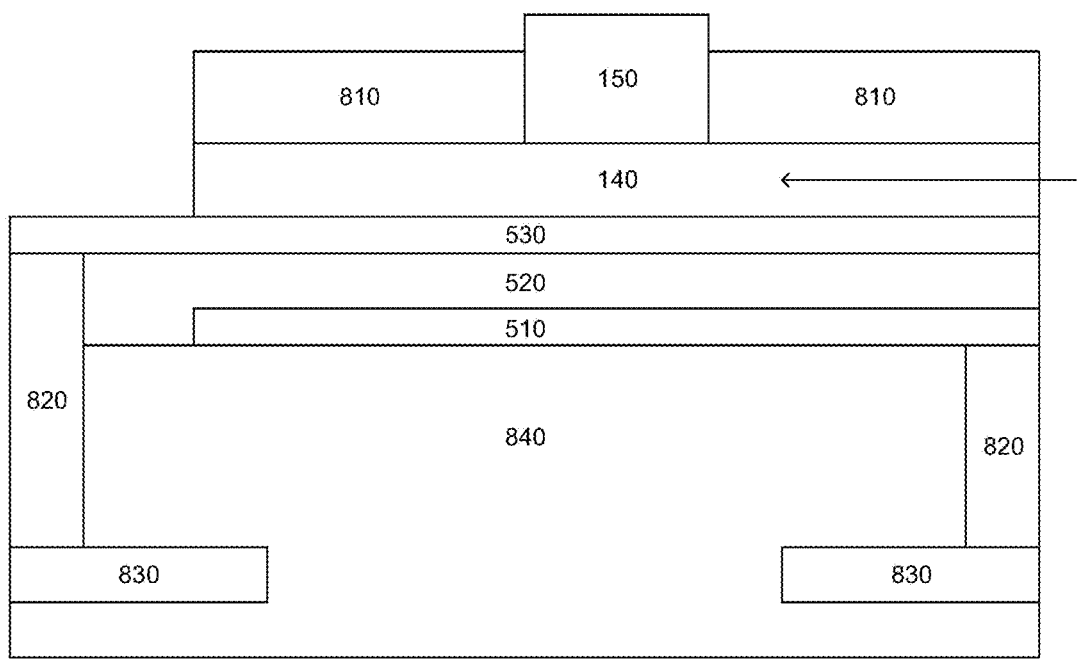
FIG. 8 schematically illustrates a system for molecular analysis fabricated using thin film semiconductor techniques.

FIG. 8 schematically illustrates a system for molecular analysis fabricated using thin film semiconductor techniques. The system 800 may be fabricated atop a silicon wafer 840. The silicon wafer may serve as a substrate for the components of the system and may also comprise circuit elements 830 and electrical connectors 820. The circuit elements may comprise control circuit elements. The circuit elements may comprise complementary metal oxide semiconductor (CMOS) circuit elements. The electrical connectors may comprise connections to a quantum well bias voltage source or channel bias voltage source (not shown) for tuning the central kinetic energy of electrons passed to the channel.

The layers 510, 520, and 530 of the single quantum well described herein may be deposited on a surface of the silicon wafer using thin film deposition techniques. The first conducting layer 510 may be deposited using metal deposition techniques to form a thin film. The first conducting layer may have a thickness of less than 1 nm, less than 2 nm, less than 3 nm, less than 4 nm, less than 5 nm, or less than 10 nm. The insulating layer 520 may be deposited using dielectric deposition techniques to form a thin film. The insulating layer may have a thickness of less than 1 nm, less than 2 nm, less than 3 nm, less than 4 nm, less than 5 nm, or less than 10 nm. The second conducting layer 530 may be deposited using metal deposition techniques to form a thin film. The second conducting layer may have a thickness of less than 1 nm, less than 2 nm, less than 3 nm, less than 4 nm, less than 5 nm, or less than 10 nm. The second conducting layer may function as the first electrode.

Although FIG. 8 refers to a single quantum well, high-order quantum wells as described herein may also be deposited using thin film deposition techniques. The (n+1)-th conducting layer of a n-tuple quantum well may function as the first electrode.

The channel 140 may be fabricated, for instance, by depositing a carbon nanotube atop the second conducting layer of the single quantum well (or the (n+1)-th conducting layer of a n-tuple quantum well). The carbon nanotube may have a diameter greater than 1 nm, greater than 2 nm, greater than 3 nm, greater than 4 nm, greater than 5 nm, or greater than 10 nm. The carbon nanotube may serve as the channel through which the liquid sample may flow. Alternatively, the carbon nanotube may be removed from the system (for instance, by etching) following the deposition of all other layers of the system.

The second electrode may be deposited atop the channel 140 using metal deposition techniques to form a thin film. The second electrode may have a thickness of less than 1 nm, less than 2 nm, less than 3 nm, less than 4 nm, less than 5 nm, less than 10 nm, less than 20 nm, less than 30 nm, less than 40 nm, less than 50 nm, or less than 100 nm. The second electrode may be surrounded by a second electrode insulating layer 810. The second electrode insulating layer may be deposited atop the channel 140 using dielectric deposition techniques to form a thin film. The second electrode insulating layer may have a thickness of less than 1 nm, less than 2 nm, less than 3 nm, less than 4 nm, less than 5 nm, less than 10 nm, less than 20 nm, less than 30 nm, less than 40 nm, less than 50 nm, or less than 100 nm.

Figure 10:
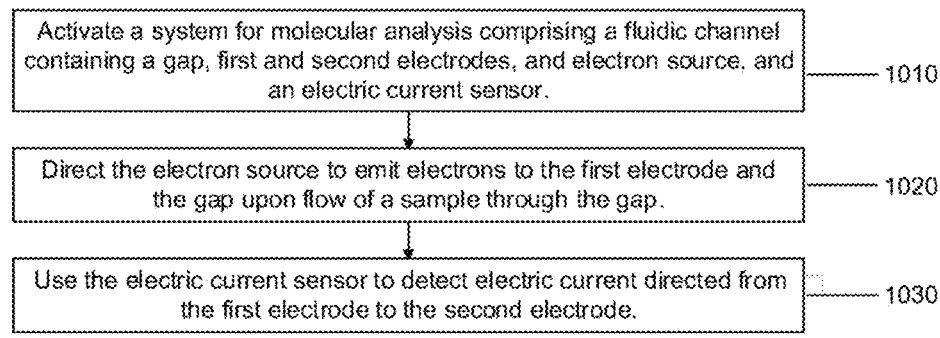
FIG. 10 shows a method for molecular analysis.

FIG. 10 shows a method 1000 for molecular analysis. In a first operation 1010, the method may comprise activating a system for molecular analysis. The system for molecular analysis may comprise a fluidic channel configured to receive a sample comprising at least one molecule. The fluidic channel may include a first electrode and a second electrode. The first electrode may be separated from the second electrode by a gap. The gap may be dimensioned to permit the sample to pass through the gap. The system for molecular analysis may further comprise an electron source. The electron source may be configured to emit electrons with a central kinetic energy and a kinetic energy distribution having a full width at half maximum (FWHM). The FWHM may be greater than 1 electron Volt (eV). The electron source may be electrically coupled to the first electrode. The system for molecular analysis may further comprise a current sensor. The current sensor may be electrically coupled to the second electrode. The current sensor may be configured to detect electric current passing from the first electrode to the second electrode. The system for molecular analysis may be any system described herein.

In a second operation 1020, the method may comprise directing the electron source to emit the electrons to the first electrode and the gap upon flow of the sample through the gap.

In a third operation 1030, the method may comprise using the current sensor to detect an electric current directed from the first electrode to the second electrode. When the at least one molecule passes through the gap, an electric current may flow from the first electrode to the second electrode. The electric current may be detected by the current sensor, indicating a presence of the at least one molecule.

Figure 15:
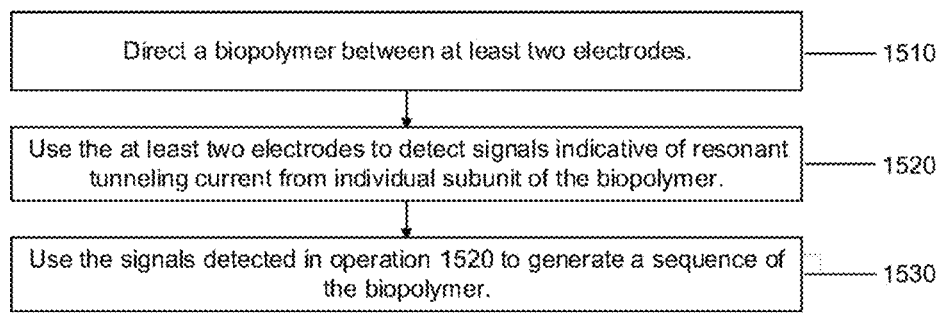
FIG. 15 shows a method for molecular analysis using resonant tunneling.

FIG. 15 shows a method 1500 for molecular analysis using resonant tunneling. In a first operation 1510, the method may comprise directing a biopolymer between at least two electrodes (such as the first and second electrodes described herein). The biopolymer may be directed between the electrodes by any mechanism described herein. For instance, biopolymer may be directed between the electrodes by electrophoresis, as described herein. The biopolymer may comprise a nucleic acid molecule. The biopolymer may comprise a protein. The biopolymer may comprise a peptide or polypeptide.

In a second operation 1520, the method may comprise using the electrodes to detect signals indicative of resonant tunneling current from individual subunits of the biopolymer. The signal indicative of resonant tunneling current may comprise any signal described herein. The individual subunits may comprise nucleosides, nucleotides, nucleoside pairs, or nucleotide pairs (for a nucleic acid). The individual subunits may comprise amino acid residues (for a protein, peptide, or polypeptide).

In a third operation 1530, the method may comprise using the signals detected in operation 1520 to generate a sequence of the biopolymer. The sequence may comprise a nucleic acid sequence. The sequence may comprise a protein sequence.

The method may achieve an accuracy of at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, at least 99.9%, at least 99.91%, at least 99.92%, at least 99.93%, at least 99.94%, at least 99.95%, at least 99.96%, at least 99.97%, at least 99.99%, or greater, over at least 10, at least 20, at least 30, at least 40, at least 50, at least 60, at least 70, at least 80, at least 90, at least 100, or greater subunits of said biopolymer without resequencing said biopolymer.

FIG. 16 shows a method 1600 for molecular analysis using non-optical detection. In a first operation 1610, the method may comprise non-optically directly detecting individual subunits of a biopolymer to generate a sequence of the biopolymer at a high accuracy over a number of subunits without resequencing. The non-optical detection may comprise any detection described herein. For instance, the non-optical detection may comprise detecting a signal indicative of resonant tunneling current, as described herein. The non-optical detection may be attained using any system described herein.

The biopolymer may be or comprise a nucleic acid molecule. The biopolymer may comprise a protein. The biopolymer may comprise a peptide or polypeptide. The individual subunits may comprise nucleosides, nucleotides, nucleoside pairs, or nucleotide pairs (for a nucleic acid). The individual subunits may comprise amino acid residues (for a protein, peptide, or polypeptide).

The method may generate a sequence of the biopolymer at an accuracy of at least 80%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, at least 99.9%, at least 99.91%, at least 99.92%, at least 99.93%, at least 99.94%, at least 99.95%, at least 99.96%, at least 99.97%, at least 99.98%, at least 99.99%, or greater over at least 5, at least 6, at least 7, at least 8, at least 9, at least 10, at least 20, at least 30, at least 40, at least 50, at least 60, at least 70, at least 80, at least 90, at least 100, at least 200, at least 300, at least 400, at least 500, at least 600, at least 700, at least 800, at least 900, at least 1,000, at least 2,000, at least 3,000, at least 4,000, at least 5,000, at least 6,000, at least 7,000, at least 8,000, at least 9,000, at least 10,000 or greater subunits, in some cases, without resequencing.

Any or more of the methods 1000, 1200, 1400, 1500, or 1600 described herein may be implemented by any system described herein.

Many variations, alterations, and adaptations based on any one or more of the methods 1000, 1200, 1400, 1500, or 1600 provided herein are possible. For example, the order of the operations of the methods 1000, 1200, 1400, 1500, or 1600 may be changed, some of the operations removed, some of the operations duplicated, and additional operations added as appropriate. Some of the operations may be performed in succession. Some of the operations may be performed in parallel. Some of the operations may be performed once. Some of the operations may be performed more than once. Some of the operations may comprise sub-operations. Some of the operations may be automated and some of the operations may be manual.

Computer Control Systems

The present disclosure provides computer control systems that are programmed to implement methods of the disclosure. FIG. 9 shows a computer system 901 that is programmed or otherwise configured to operate a system for molecular analysis described herein. The computer system 901 can regulate various aspects of the present disclosure. The computer system 901 can be an electronic device of a user or a computer system that is remotely located with respect to the electronic device. The electronic device can be a mobile electronic device.

The computer system 901 includes a central processing unit (CPU, also "processor" and "computer processor" herein) 905, which can be a single core or multi core processor, or a plurality of processors for parallel processing. The computer system 901 also includes memory or memory location 910 (e.g., random-access memory, read-only memory, flash memory), electronic storage unit 915 (e.g., hard disk), communication interface 920 (e.g., network adapter) for communicating with one or more other systems, and peripheral devices 925, such as cache, other memory, data storage and/or electronic display adapters. The memory 910, storage unit 915, interface 920 and peripheral devices 925 are in communication with the CPU 905 through a communication bus (solid lines), such as a motherboard. The storage unit 915 can be a data storage unit (or data repository) for storing data. The computer system 901 can be operatively coupled to a computer network ("network") 930 with the aid of the communication interface 920. The network 930 can be the Internet, an internet and/or extranet, or an intranet and/or extranet that is in communication with the Internet. The network 930 in some cases is a telecommunication and/or data network. The network 930 can include one or more computer servers, which can enable distributed computing, such as cloud computing. The network 930, in some cases with the aid of the computer system 901, can implement a peer-to-peer network, which may enable devices coupled to the computer system 901 to behave as a client or a server.

The CPU 905 can execute a sequence of machine-readable instructions, which can be embodied in a program or software. The instructions may be stored in a memory location, such as the memory 910. The instructions can be directed to the CPU 905, which can subsequently program or otherwise configure the CPU 905 to implement methods of the present disclosure. Examples of operations performed by the CPU 905 can include fetch, decode, execute, and writeback.

The CPU 905 can be part of a circuit, such as an integrated circuit. One or more other components of the system 901 can be included in the circuit. In some cases, the circuit is an application specific integrated circuit (ASIC).

The storage unit 915 can store files, such as drivers, libraries and saved programs. The storage unit 915 can store user data, e.g., user preferences and user programs. The computer system 901 in some cases can include one or more additional data storage units that are external to the computer system 901, such as located on a remote server that is in communication with the computer system 901 through an intranet or the Internet.

The computer system 901 can communicate with one or more remote computer systems through the network 930. For instance, the computer system 901 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 901 via the network 930.

Methods as described herein can be implemented by way of machine (e.g., computer processor) executable code stored on an electronic storage location of the computer system 901, such as, for example, on the memory 910 or electronic storage unit 915. The machine executable or machine readable code can be provided in the form of software. During use, the code can be executed by the processor 905. In some cases, the code can be retrieved from the storage unit 915 and stored on the memory 910 for ready access by the processor 905. In some situations, the electronic storage unit 915 can be precluded, and machine-executable instructions are stored on memory 910.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 901, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 901 can include or be in communication with an electronic display 935 that comprises a user interface (UI) 940. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 905. The algorithm can, for example, determine a macromolecular sequence based on electric currents detected by the electric current sensors described herein.

EXAMPLES

Example 1

Circuit Architectures

FIG. 17A shows a first example of a circuit architecture for a system 1700a for molecular analysis. The system 1700a may comprise any or all elements of any system described herein. For instance, as shown in FIG. 17A, the system may comprise a first electrode (or emitter) 120, a fluid channel 130, and second electrode (or collector) 140, respectively. The first electrode may function as the first conducting region 510 of a quantum well described herein. The system may further comprise an insulating region 520 and a second conducting region (or base) 530 of a quantum well described herein. The system may be assembled in a vertical (out of the page in FIG. 17A) fashion using deposition and removal of layers of components following semiconductor processing protocols described herein. For instance, the system may be assembled using metal-insulator-metal (MIM) semiconductor techniques.

For instance, the system may be assembled such that the quantum well is formed with the emitter beneath the base and the base beneath the collectors. The channel may be formed above the collectors. The channel may comprise a carbon nanotube. The system may further comprise positive and negative electrophoresis electrodes 170 and 180, respectively, as described herein.

The system may further comprise an electric shield 190. The electric shield may be configured to reduce electric noise received by the collector due to electromagnetic coupling between any elements of the system.

Though depicted as comprising a single collector and a single shield in FIG. 17A, the system may comprise any number of collectors and any number of shields, such as at least 1, at least 2, at least 3, at least 4, at least 5, at least 6, at least 7, at least 8, at least 9, at least 10, at least 20, at least 30, at least 40, at least 50, at least 60, at least 70, at least 80, at least 90, at least 100, at least 200, at least 300, at least 400, at least 500, at least 600, at least 700, at least 800, at least 900, or at least 1,000 collectors, and at least 1, at least 2, at least 3, at least 4, at least 5, at least 6, at least 7, at least 8, at least 9, at least 10, at least 20, at least 30, at least 40, at least 50, at least 60, at least 70, at least 80, at least 90, at least 100, at least 200, at least 300, at least 400, at least 500, at least 600, at least 700, at least 800, at least 900, or at least 1,000 shields. The system may comprise a number of collectors or shields that is within a range defined by any two of the preceding values. In some instances, the collectors and shields may be arranged in an alternating manner, with a first collector, a first shield, a second collector, a second shield, and so on, arranged in that order. Such a configuration may reduce electric noise received by the first and second collectors. The alternating manner may be repeated as necessary for any number of collectors and any number of shields.

Though depicted as comprising a single quantum well in FIG. 17A, the system 1700a may comprise any quantum well described herein, such as a double quantum well, triple quantum well, or higher-order quantum well.

The system may be formed on a substrate 1710. The substrate may comprise a metal, non-metal, semiconductor, plastic, or any other type of substrate. For instance, the substrate may comprise silicon or glass.

Figure 17B:
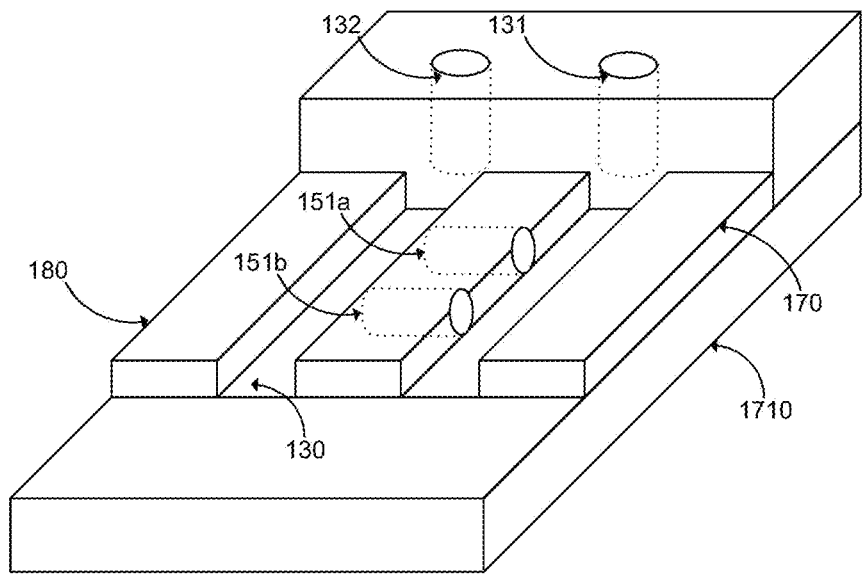
FIG. 17B shows an orthographic view of a second example of a circuit architecture for a system for molecular analysis.

FIG. 17B shows an orthographic view of a second example of a circuit architecture for a system 1700b for molecular analysis. The system 1700b may comprise any or all elements of any system described herein. For instance, as shown in FIG. 17B, the system may comprise a channel 130. The channel may comprise an inlet 131 and an outlet 132. The system may comprise first and second current sensors 150a and 150b (one or both of which may be similar to current sensor 150 described herein), respectively. Though depicted as comprising two current sensors in FIG. 17B, the system may comprise any number of current sensors or sub-sensors described herein, such as at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 current sensors or sub-sensors. The system may further comprise positive and negative electrophoresis electrodes 170 and 180, respectively, as described herein.

Figure 17C:
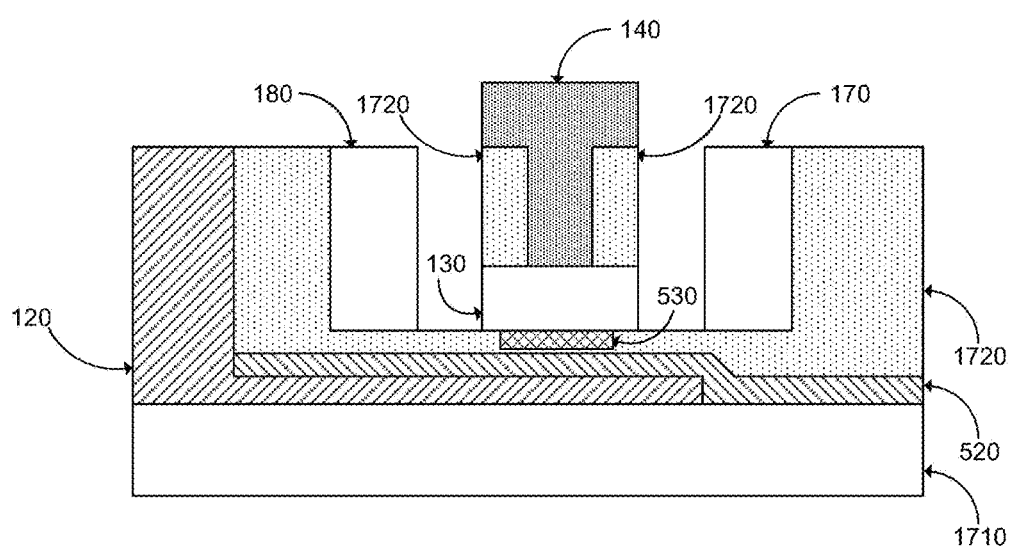
FIG. 17C shows a side view of a second example of a circuit architecture for a system for molecular analysis.

FIG. 17C shows a side view of the second example of the circuit architecture for the system 1700b for molecular analysis. As shown in FIG. 17C, the system may further comprise a first electrode (or emitter) 120 and a second electrode (or collector) 140. The first electrode may function as the first conducting region 510 of a quantum well described herein. The system may further comprise an insulating region 520 and a second conducting region (or base) 530 of a quantum well described herein. The system may further comprise insulating regions 1720. The insulating regions may electrically isolate components of the system from one another. The system may be assembled in a vertical (out of the page in FIG. 17C) fashion using deposition and removal of layers of components following semiconductor processing protocols described herein. For instance, the system may be assembled using microelectromechanical systems (MEMS) or nanoelectromechanical systems (NEMS) semiconductor techniques.

Though depicted as comprising a single quantum well in FIGS. 17B and 17C, the system 1700a may comprise other types of quantum wells, including any quantum well described herein, such as a double quantum well, triple quantum well, or higher-order quantum well. The system 1700a may comprise at least 1, 2, 3, 4, 5, 6, 7, 8, 9, 10, or more quantum wells.

The system may be formed on a substrate 1710. The substrate may comprise a metal, non-metal, semiconductor, plastic, or any other type of substrate. For instance, the substrate may comprise silicon or glass.

Example 2

Quantum Well Simulations

Figure 18A:
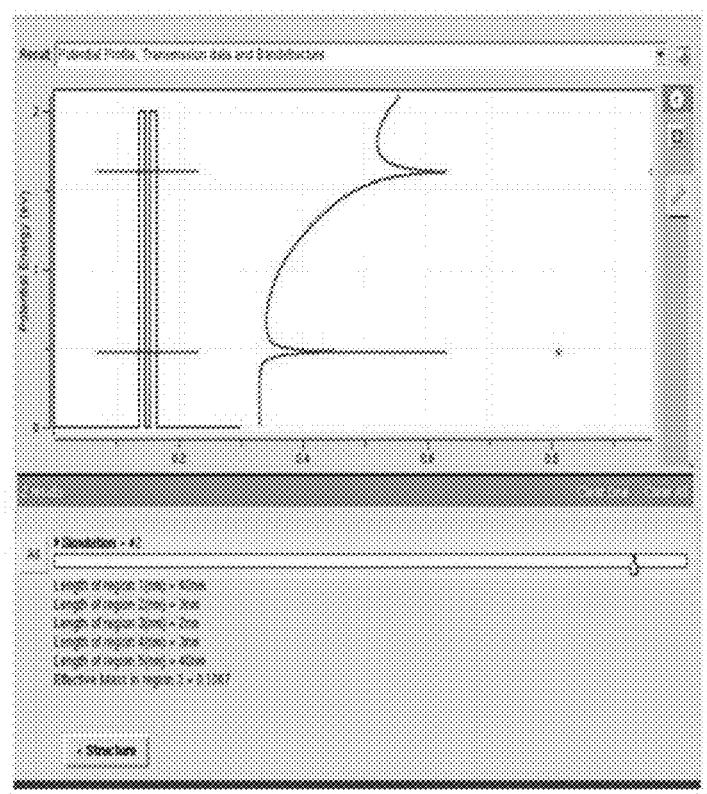
FIG. 18A shows simulated energy levels for a first exemplary double quantum well.

FIG. 18A shows simulated energy levels for a first exemplary double quantum well comprising a first conducting region (region 1 in FIG. 18A), a first insulating region (region 2), a second conducting region (region 3), a second insulating region (region 4), and a third conducting region (region 5), with the regions arranged in that order. The first and third conducting regions each have a thickness of 40 nm. The first and second insulating regions each have a thickness of 3 nm. The second conducting region has a thickness of 2 nm. The first and second insulating regions each have a work function of 2 electron Volts (eV). The first, second, and third conducting regions each have an effective mass of 0.1067 electron rest masses. The first and second insulating regions each have an effective mass of 0.067 electron rest masses. As seen in FIG. 18A, the double quantum well has 2 energy eigenvalues at approximately 0.5 eV and 1.6 eV.

Figure 18B:
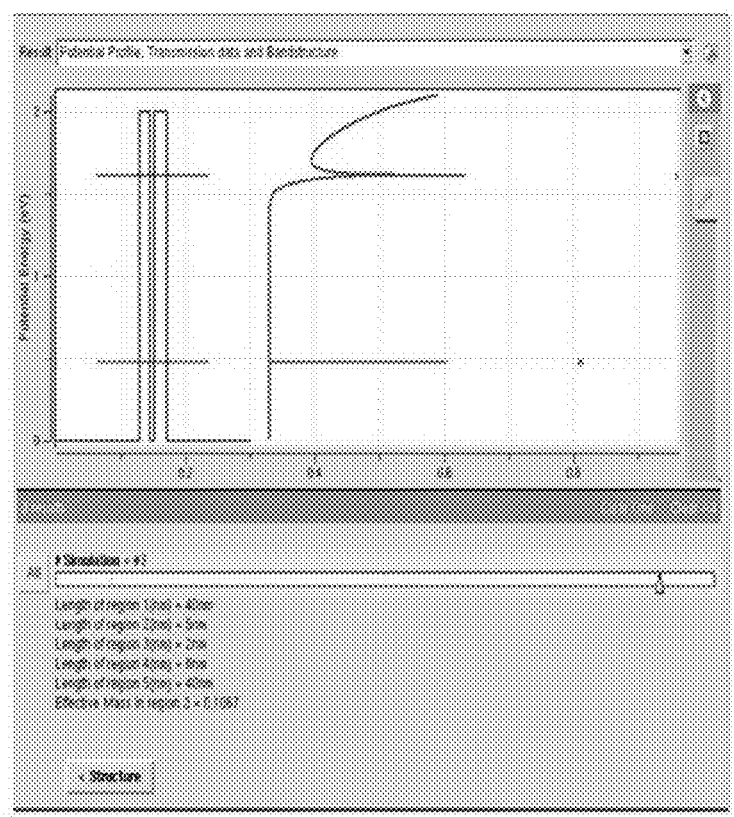
FIG. 18B shows simulated energy levels for a second exemplary double quantum well.

FIG. 18B shows simulated energy levels for a second exemplary double quantum well comprising a first conducting region (region 1 in FIG. 18B), a first insulating region (region 2), a second conducting region (region 3), a second insulating region (region 4), and a third conducting region (region 5), with the regions arranged in that order. The first and third conducting regions each have a thickness of 40 nm. The first and second insulating regions each have a thickness of 5 nm. The second conducting region has a thickness of 2 nm. The first and second insulating regions each have a work function of 2 electron Volts (eV). The first, second, and third conducting regions each have an effective mass of 0.1067 electron rest masses. The first and second insulating regions each have an effective mass of 0.067 electron rest masses. As seen in FIG. 18B, the double quantum well has 2 energy eigenvalues at approximately 0.5 eV and 1.6 eV. Thus, it can be seen that increasing the thicknesses of the first and second insulating regions has little effect on the energy levels of the double quantum well.

Figure 18C:
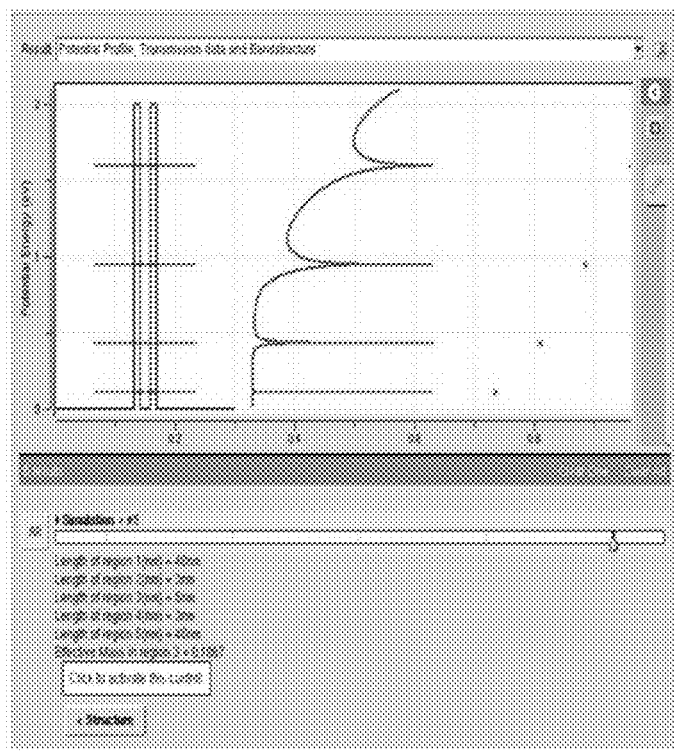
FIG. 18C shows simulated energy levels for a third exemplary double quantum well.

FIG. 18C shows simulated energy levels for a third exemplary double quantum well comprising a first conducting region (region 1 in FIG. 18C), a first insulating region (region 2), a second conducting region (region 3), a second insulating region (region 4), and a third conducting region (region 5), with the regions arranged in that order. The first and third conducting regions each have a thickness of 40 nm. The first and second insulating regions each have a thickness of 3 nm. The second conducting region has a thickness of 5 nm. The first and second insulating regions each have a work function of 2 electron Volts (eV). The first, second, and third conducting regions each have an effective mass of 0.1067 electron rest masses. The first and second insulating regions each have an effective mass of 0.067 electron rest masses. As seen in FIG. 18C, the double quantum well has 4 energy eigenvalues at approximately 0.10 eV, 0.41 eV, 0.91 eV, and 1.57 eV. Thus it can be seen that increasing the thickness of the second conducting region increases the number of eigenvalues and decreases the spacing between adjacent eigenvalues.

Figure 18D:
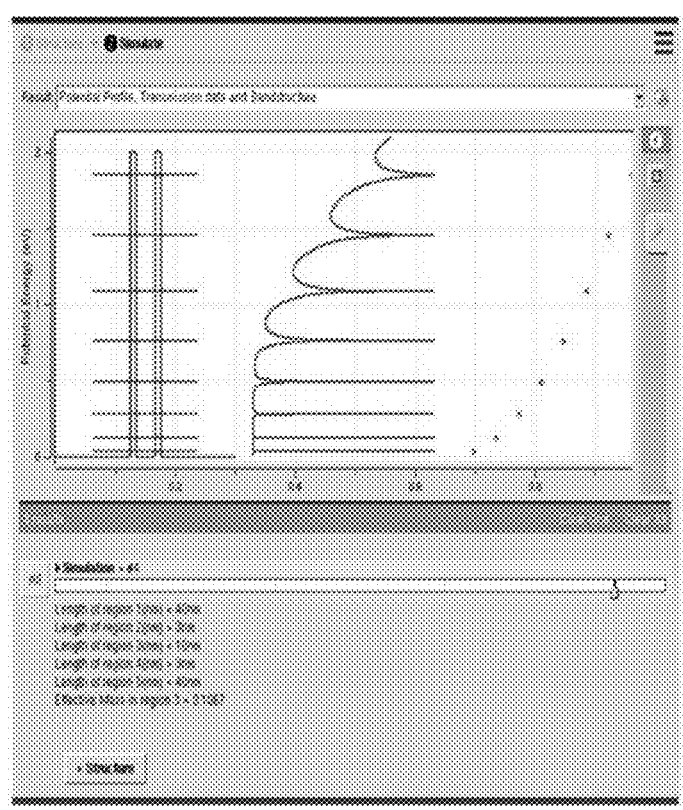
FIG. 18D shows simulated energy levels for a fourth exemplary double quantum well.

FIG. 18D shows simulated energy levels for a fourth exemplary double quantum well comprising a first conducting region (region 1 in FIG. 18D), a first insulating region (region 2), a second conducting region (region 3), a second insulating region (region 4), and a third conducting region (region 5), with the regions arranged in that order. The first and third conducting regions each have a thickness of 40 nm. The first and second insulating regions each have a thickness of 3 nm. The second conducting region has a thickness of 10 nm. The first and second insulating regions each have a work function of 2 electron Volts (eV). The first, second, and third conducting regions each have an effective mass of 0.1067 electron rest masses. The first and second insulating regions each have an effective mass of 0.067 electron rest masses. As seen in FIG. 18D, the double quantum well has 8 energy eigenvalues at approximately 0.03 eV, 0.12 eV, 0.27 eV, 0.48 eV, 0.74 eV, 1.07 eV, 1.44 eV, and 1.84 eV. Thus it can be seen that further increasing the thickness of the second conducting region further increases the number of eigenvalues and further decreases the spacing between adjacent eigenvalues.

Figure 18E:
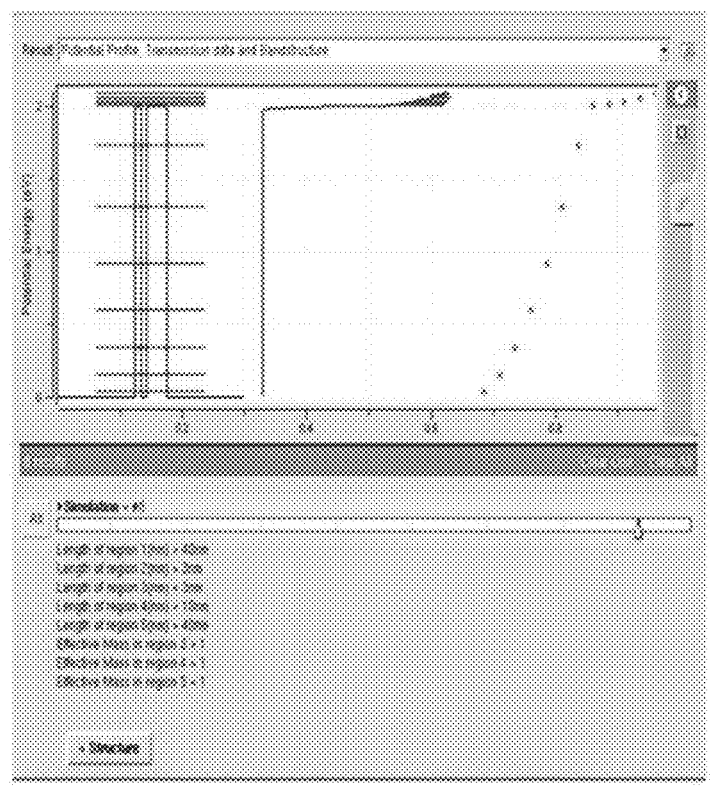
FIG. 18E shows simulated energy levels for a fifth exemplary double quantum well.

FIG. 18E shows simulated energy levels for a fifth exemplary double quantum well comprising a first conducting region (region 1 in FIG. 18E), a first insulating region (region 2), a second conducting region (region 3), a second insulating region (region 4), and a third conducting region (region 5), with the regions arranged in that order. The first and third conducting regions each have a thickness of 40 nm. The first insulating region has a thickness of 3 nm. The second insulating region has a thickness of 10 nm. The second conducting region has a thickness of 3 nm. The first and second insulating regions each have a work function of 2 electron Volts (eV). The first, second, and third conducting regions each have an effective mass of 1 electron rest mass. The first and second insulating regions each have an effective mass of 1 electron rest mass. As seen in FIG. 18E, the double quantum well has 12 energy eigenvalues at approximately 0.04 eV, 0.15 eV, 0.34 eV, 0.59 eV, 0.92 eV, 1.30 eV, 1.73 eV, 2.10 eV, 2.17 eV, 2.14 eV, 2.16 eV, and 2.20 eV. Thus it can be seen that increasing the effective masses of the conducting and insulation regions further the number of eigenvalues and decreases the spacing between adjacent eigenvalues.

Figure 18F:
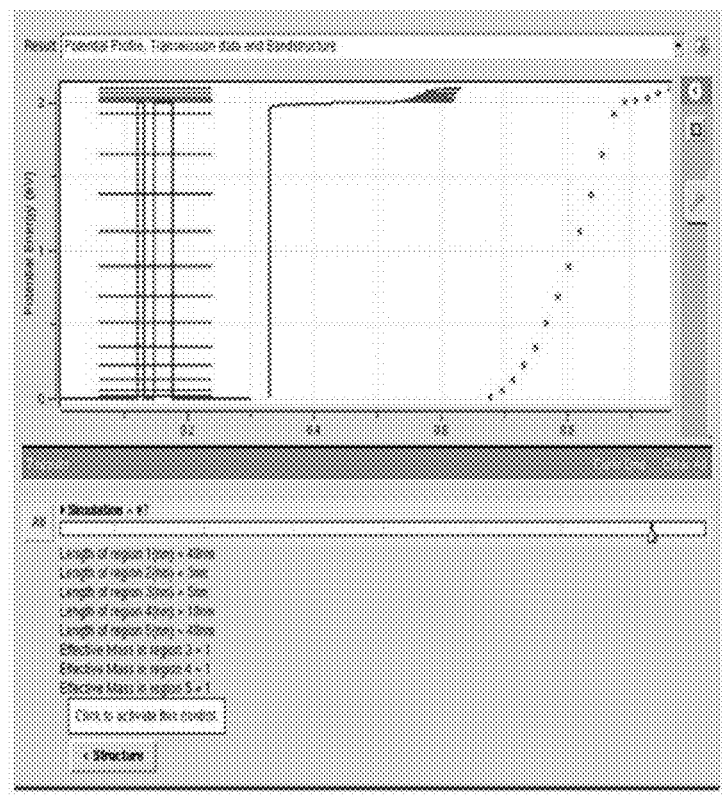
FIG. 18F shows simulated energy levels for a sixth exemplary double quantum well.

FIG. 18F shows simulated energy levels for a sixth exemplary double quantum well comprising a first conducting region (region 1 in FIG. 18F), a first insulating region (region 2), a second conducting region (region 3), a second insulating region (region 4), and a third conducting region (region 5), with the regions arranged in that order. The first and third conducting regions each have a thickness of 40 nm. The first insulating region has a thickness of 3 nm. The second insulating region has a thickness of 10 nm. The second conducting region has a thickness of 5 nm. The first and second insulating regions each have a work function of 2 electron Volts (eV). The first, second, and third conducting regions each have an effective mass of 1 electron rest mass. The first and second insulating regions each have an effective mass of 1 electron rest mass. As seen in FIG. 18F, the double quantum well has 17 energy eigenvalues at approximately 0.02 eV, 0.06 eV, 0.13 eV, 0.23 eV, 0.35 eV, 0.50 eV, 0.68 eV, 0.89 eV, 1.12 eV, 1.37 eV, 1.64 eV, 1.91 eV, 2.00 eV, 2.02 eV, 2.03 eV, 2.06 eV, and 2.09 eV. Thus it can be seen that increasing the thickness of the second conducting region increases the number of eigenvalues and decreases the spacing between adjacent eigenvalues.

Figure 18G:
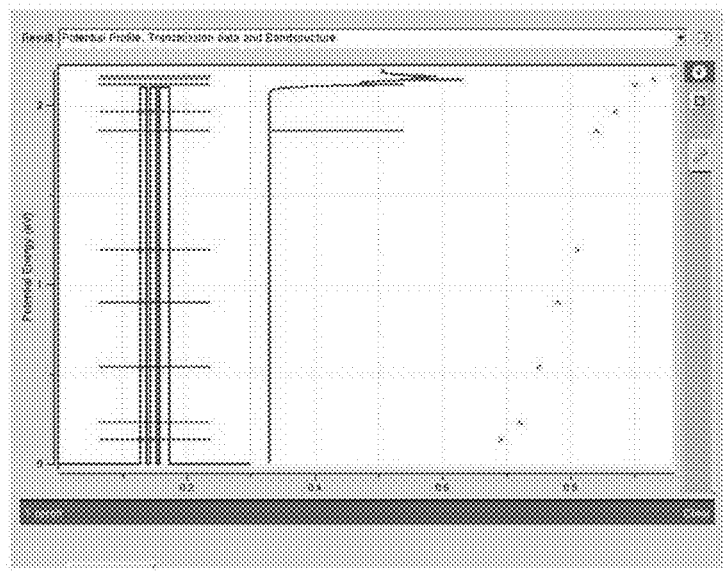
FIG. 18G shows simulated energy levels for an exemplary triple quantum well.

FIG. 18G shows simulated energy levels for a first exemplary triple quantum well comprising a first conducting region, a first insulating region, a second conducting region, a second insulating region, a third conducting region, a third insulating region, and a fourth conducting region, with the regions arranged in that order. The first and fourth conducting regions each have a thickness of 40 nm. The second and third conducting regions each have a thickness of 5 nm. The first, second, and third insulating regions each have a thickness of 3 nm. The first, second, and insulating regions each have a work function of 2 electron Volts (eV). The first, second, third, and fourth conducting regions each have an effective mass of 1 electron rest mass. The first and second insulating regions each have an effective mass of 1 electron rest mass. As seen in FIG. 18G, the double quantum well has 10 energy eigenvalues at approximately 0.14 eV, 0.23 eV, 0.54 eV, 0.90 eV, 1.20 eV, 1.86 eV, 1.96 eV, 2.12 eV, 2.14 eV, and 2.16 eV.

Example 3

Pseudo-Code for Sweeping Over Voltages to Detect 4 Nucleotide Bases define the variables:

```
moving_speed = 1
DNA_position = 0
time = [0]
detector_voltage = [V1, V2, V3, V4]
base_current = np.array([I1, I2, I3, I4]) #nA, detection current of base A
base_type = np.array(['A', 'B', 'C', 'D'])
DNA_chain = [ ]
#define a function to read the time and current
def read(lock_in_integ_time, Voltage, frequency):
    read_current = [ ]
    read_time = [ ]
    for i in range(int(lock_in_integ_time*frequency)):
        read_current.append(current)
        read_time.append(time)
    average_current = np.mean(read_current)
    duration = read_time[-1] – read_time[0]
    return duration, read_time[-1], average_current
def detector(Voltage):
    chain=np.array([ ])
    _, read_time, read_current = read(lock_in_integ_time, Voltage, frequency)
    if (read_current != 0) and (read_current % base_current[detector_voltage==Voltage] == 0):
        chain = np.append(chain, base_type[detector_voltage==Voltage])
    else:
        chain = np.append(chain, [0])
    return chain
current = [I1, I2, I3, I4]
chain = {0:np.array([ ]),1:np.array([ ]),2:np.array([ ]),3:np.array([ ])}
DNA_chain = np.array([ ])
while ((current[0] != 0) or (current[1] != 0) or (current[2] != 0) or (current[3] != 0)):
    DNA_position += 1
    for i in range(len(detector_voltage)):
        Voltage = detector_voltage[i]
        current[i], chain[i] = detector(Voltage, chain[i], current[i])
DNA_chain = np.append(DNA_chain, chain[0]+chain[1]+chain[2]+chain[3])
```

Example 4

Pseudo-Code for Detecting a Single Nucleotide Base calibration of each detector, to find the width of it:
pass a chain of single type base, and set the voltage of all detectors to detect that base, for example 'A':

```
base_type = "A"
detected_current1=[ ]
for i in range(2):
    DNA_position += 1
    _, read_time, read_curren1t = read(lock_in_integ_time, Voltage1, frequency)
    detected_current1.append(read_current1)
while detected_current1[-1] != detected_curren1[-2]:
    DNA_position += 1
    _, read_time, read_current1 = read(lock_in_integ_time, Voltage1, frequency)
    detected_current1.append(read_current1)
    detector_width = int(read_current1/base_current)
#to detect the separation between 2 detectors:
#pass a chain of single type base, and set the voltage of all detectors to detect that base, for example 'A':
separation=0
DNA_position += 1
_, read_time, read_current2 = read(lock_in_integ time, Voltage2, frequency)
while read_current2 == 0:
    separation += 1
    DNA_position += 1
    _, read_time, read_current2 = read(lock_in_integ_time, Voltage2, frequency)
def detector(Voltage):
    chain=np.array([ ])
```

```
_, read_time, read_current = read(lock_in_integ_time, Voltage, frequency)
    if (read _current != 0) and (read_current % base_current[detector_voltage==Voltage]
== 0):
        chain = np.append(chain, base_type[detector_voltage==Voltage])
    else:
        chain = np.append(chain, [0])
    return chain
DNA_chain = np.array(['init']*16)
while DNA_chain[-16:] != [0]*16:
    for i in range(16):
        chain_A = detector(V1)
        chain_B = detector(V2)
        chain_C = detector(V3)
        chain_D = detector(V4)
    DNA_chain = np.append(DNA_chain, chain_A+chain_B+chain_C+chain_D)
```

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A system for molecular analysis, comprising: a fluidic channel configured to receive a sample comprising at least one molecule, wherein the fluidic channel includes a first electrode and a second electrode, wherein the first electrode is separated from the second electrode by a gap, which gap is dimensioned to permit the sample to pass through the gap; an electron source configured to emit electrons with a central kinetic energy and a kinetic energy distribution having a full width at half maximum (FWHM) of no greater than 1 electron Volt (eV), wherein the electron source is electrically coupled to the first electrode; a current sensor electrically coupled to the second electrode and configured to detect electric current passing from the first electrode to the second electrode; and a controller coupled to the electron source and the current sensor, wherein the controller is configured to: (i) direct the electron source to emit the electrons to the first electrode and the gap upon flow of the sample through the gap, and (ii) use the current sensor to detect an electric current directed from the first electrode to the second electrode, wherein when the at least one molecule passes through the gap, an electric current flows from the first electrode to the second electrodes and is detected by the current sensor, indicating a presence of the at least one molecule, wherein the electron source comprises a thermal electron source and a quantum tunneling filter structure, wherein the quantum tunneling filter structure comprises a first metallic thin film, a dielectric thin film, and a second metallic thin film, wherein the first metallic thin film and second metallic thin films comprise a material selected from a group consisting of platinum, gold, silver, copper, titanium nitride, and cobalt silicide, wherein the dielectric thin film comprises a material selected from a group consisting of silicon oxide ($SiO_x$), aluminum oxide ($Al_xO_y$) silicon nitride ($Si_3N_4$), and calcium fluoride (CaF), wherein the thermal electron source produces a population of electrons having a thermal distribution of kinetic energies, wherein the quantum tunneling filter structure utilizes a quantum tunneling phenomenon to filter the electrons thermally distributed by the thermal electron source, wherein the quantum tunneling filter structure transmits the electrons to an appreciable extent if they have a kinetic energy that matches a resonance condition of a quantum well system, wherein the fluidic channel is configured to receive a liquid sample, wherein the liquid sample flows along a length of the fluidic channel past a gap between the first electrode and the second electrode, wherein the quantum tunneling filter structure comprises a double quantum well structure, wherein the double quantum well structure is biased by a quantum well bias voltage source, wherein the fluidic channel is biased by a channel bias voltage source, wherein the double quantum well structure has at least 17 energy eigenvalues at about 0.02 eV, 0.06 eV, 0.13 eV, 0.23 eV, 0.35 eV, 0.50 eV, 0.68 eV, 0.89 eV, 1.12 eV, 1.37 eV, 1.64 eV, 1.91 eV, 2.00 eV, 2.02 eV, 2.03 eV, 2.06 eV, and 2.09 eV.

2. The system of claim 1, wherein the controller is configured to bias the first electrode by a first electric potential and to bias the second electrode by a second electric potential.

3. The system of claim 2, wherein the first and second electric potentials determine the central kinetic energy of the emitted electrons.

4. The system of claim 1, wherein the electrons are emitted with a kinetic energy distribution having a full width at half maximum (FWHM) of no greater than 0.1 eV.

5. The system of claim 1, wherein the electrons are emitted with a kinetic energy distribution having a central energy that corresponds to a highest occupied molecular orbital (HOMO) to lowest unoccupied molecular orbital (LUMO) transition energy of the at least one molecule or the portion of the at least one molecule.

6. The system of claim 5, wherein the electrons are emitted with a kinetic energy distribution having a central energy that corresponds to a HOMO to LUMO transition energy of a nucleoside, nucleotide, nucleoside pair, or nucleotide pair of the sample.

7. The system of claim 1, wherein the width of the fluidic channel is at least 1 nm.

8. The system of claim 1, wherein the current sensor is configured to detect a nucleoside, nucleotide, nucleoside pair, or nucleotide pair of only a single type.

9. The system of claim 1, wherein the current sensor comprises a plurality of current sub-sensors.

10. The system of claim 9, wherein each sub-sensor of the plurality is configured to detect a nucleoside, nucleotide, nucleoside pair, or nucleotide pair of a single type.

11. The system of claim 9, wherein each sub-sensor of the plurality is configured to detect a methylated nucleoside, methylated nucleotide, methylated nucleoside pair, or methylated nucleotide pair of a single type.

12. The system of claim 1, wherein the current sensor is configured to detect nucleosides, nucleotides, nucleoside pairs, or nucleotide pairs of a plurality of types, which plurality is less than all types of nucleosides, nucleotides, nucleoside pairs, or nucleotide pairs.

13. The system of claim 1, wherein the current sensor is configured to detect methylated nucleosides, methylated nucleotides, methylated nucleoside pairs, or methylated nucleotide pairs of a plurality of types, which plurality is less than all types of methylated nucleotides, methylated nucleoside pairs, or methylated nucleotide pairs.

14. The system of claim 1, further comprising a positive electrophoresis electrode located at a first position along a length of the channel and a negative electrophoresis electrode located at a second position along the length of the channel, the positive and negative electrophoresis electrodes configured to advance the sample along all or a part of the length of the channel by electrophoresis.

15. A method for molecular analysis, comprising: (a) activating a system comprising (i) a fluidic channel configured to receive a sample comprising at least one molecule, wherein the fluidic channel includes a first electrode and a second electrode, wherein the first electrode is separated from the second electrode by a gap, which gap is dimensioned to permit the sample to pass through the gap; (ii) an electron source configured to emit electrons with a central kinetic energy and a kinetic energy distribution having a full width at half maximum (FWHM) of no greater than 1 electron Volt (eV), wherein the electron source is electrically coupled to the first electrode; and (iii) a current sensor electrically coupled to the second electrode and configured to detect electric current passing from the first electrode to the second electrode; (b) directing the electron source to emit the electrons to the first electrode and the gap upon flow of the sample through the gap; and (c) using the current sensor to detect an electric current directed from the first electrode to the second electrode, wherein when the at least one molecule passes through the gap, an electric current flows from the first electrode to the second electrodes and is detected by the current sensor, indicating a presence of the at least one molecule, wherein the electron source comprises a thermal electron source and a quantum tunneling filter structure, wherein the quantum tunneling filter structure comprises a first metallic thin film, a dielectric thin film, and a second metallic thin film, wherein the first metallic thin film and second metallic thin films comprise a material selected from a group consisting of platinum, gold, silver, copper, titanium nitride, and cobalt silicide, wherein the dielectric thin film comprises a material selected from a group consisting of silicon oxide ($SiO_x$), aluminum oxide ($Al_xO_y$), silicon nitride ($Si_3N_4$), and calcium fluoride (CaF), wherein the thermal electron source produces a population of electrons having a thermal distribution of kinetic energies, wherein the quantum tunneling filter structure utilizes a quantum tunneling phenomenon to filter the electrons thermally distributed by the thermal electron source, wherein the quantum tunneling filter structure transmits the electrons to an appreciable extent if they have a kinetic energy that matches a resonance condition of a quantum well system, wherein the fluidic channel is configured to receive a liquid sample, wherein the liquid sample flows along a length of the fluidic channel past a gap between the first electrode and the second electrode, wherein the quantum tunneling filter structure comprises a double quantum well structure, wherein the double quantum well structure is biased by a quantum well bias voltage source, wherein the fluidic channel is biased by a channel bias voltage source, wherein the double quantum well structure has at least 17 energy eigenvalues at about 0.02 eV, 0.06 eV, 0.13 eV, 0.23 eV, 0.35 eV, 0.50 eV, 0.68 eV, 0.89 eV, 1.12 eV, 1.37 eV, 1.64 eV, 1.91 eV, 2.00 eV, 2.02 eV, 2.03 eV, 2.06 eV, and 2.09 eV.

16. The method of claim 15, wherein the system further comprises a positive electrophoresis electrode located at a first position along a length of the channel and a negative electrophoresis electrode located at a second position along the length of the channel, the positive and negative electrophoresis electrodes configured to advance the sample along all or a part of the length of the channel by electrophoresis.

17. The method of claim 15, further comprising advancing the sample along all or a part of the length of the channel by electrophoresis.

* * * * *